(12) United States Patent
Kumar et al.

(10) Patent No.: US 7,902,317 B2
(45) Date of Patent: *Mar. 8, 2011

(54) SYNTHESIS OF ANILINE AND PHENOL-BASED ANTIOXIDANT MACROMONOMERS AND CORRESPONDING POLYMERS

(75) Inventors: Rajesh Kumar, Dracut, MA (US); Suizhou Yang, Lowell, MA (US); Ashok L. Cholli, Chelmsford, MA (US)

(73) Assignee: Polnox Corporation, Lowell, MA (US)

( * ) Notice: Subject to any disclaimer, the term of this patent is extended or adjusted under 35 U.S.C. 154(b) by 304 days.

This patent is subject to a terminal disclaimer.

(21) Appl. No.: 11/293,844

(22) Filed: Dec. 2, 2005

(65) Prior Publication Data

US 2006/0128931 A1 Jun. 15, 2006

Related U.S. Application Data

(60) Provisional application No. 60/633,196, filed on Dec. 3, 2004.

(51) Int. Cl.
*C08G 63/00* (2006.01)
*C08G 61/02* (2006.01)
(52) U.S. Cl. ............ 528/183; 528/86; 562/357; 562/442
(58) Field of Classification Search .................. 562/357, 562/442; 528/86, 183
See application file for complete search history.

(56) References Cited

U.S. PATENT DOCUMENTS

| | | | |
|---|---|---|---|
| 3,116,305 A | 12/1963 | Morris et al. |
| 3,294,836 A | 12/1966 | Peterson et al. |
| 3,441,545 A | 4/1969 | Blatz et al. |
| 3,459,704 A | 8/1969 | Peterson et al. |
| 3,557,245 A | 1/1971 | Phillips et al. |
| 3,632,785 A | 1/1972 | Bornstein |
| 3,645,970 A | 2/1972 | Kleiner |
| 3,649,667 A | 3/1972 | Song et al. |
| 3,655,831 A | 4/1972 | Friedman |
| 3,870,680 A | 3/1975 | Schurdak |
| 3,907,939 A | 9/1975 | Robin et al. |
| 3,953,402 A | 4/1976 | Kline |
| 3,965,039 A | 6/1976 | Chaplits et al. |
| 3,983,091 A | 9/1976 | Gloth et al. |
| 3,994,828 A | 11/1976 | Zaffaroni |
| 3,996,160 A | 12/1976 | Dale et al. |
| 3,996,198 A | 12/1976 | Wang et al. |
| 4,054,676 A | 10/1977 | Weinshenker et al. |
| 4,094,857 A | 6/1978 | Wolfe, Jr. |
| 4,096,319 A | 6/1978 | Willette et al. |
| 4,097,464 A | 6/1978 | Kline |
| 4,098,829 A | 7/1978 | Weinshenker et al. |
| 4,107,144 A | 8/1978 | Russell et al. |
| 4,136,055 A | 1/1979 | Lyons |
| 4,202,816 A | 5/1980 | Moser et al. |
| 4,205,151 A | 5/1980 | Dale et al. |
| 4,213,892 A | 7/1980 | Scott |
| 4,219,453 A | 8/1980 | Sakurai et al. |
| 4,267,358 A | 5/1981 | Hechenbleikner et al. |
| 4,281,192 A | 7/1981 | Jacquet et al. |
| 4,283,572 A | 8/1981 | Klicker |
| 4,317,933 A | 3/1982 | Parker |
| 4,341,879 A | 7/1982 | Sugio et al. |
| 4,355,148 A | 10/1982 | Layer et al. |
| 4,377,666 A | 3/1983 | Farrar |
| 4,380,554 A | 4/1983 | Serres, Jr. |
| 4,447,657 A | 5/1984 | Firth et al. |
| 4,465,871 A | 8/1984 | Firth et al. |
| 4,510,296 A | 4/1985 | Hergenrother |
| 4,511,491 A | 4/1985 | Ishii et al. |
| 4,690,995 A | 9/1987 | Keskey et al. |
| 4,761,247 A | 8/1988 | Rei et al. |
| 4,824,929 A | 4/1989 | Arimatsu et al. |
| 4,849,503 A | 7/1989 | Cotter et al. |
| 4,855,345 A | 8/1989 | Rosenberger et al. |
| 4,857,596 A | 8/1989 | MacLeay et al. |
| 4,870,214 A | 9/1989 | Mina et al. |
| 4,894,263 A | 1/1990 | Dubois et al. |
| 4,897,438 A | 1/1990 | Kikuchi et al. |
| 4,900,671 A | 2/1990 | Pokora et al. |
| 4,925,591 A | 5/1990 | Nakauchi et al. |
| 4,968,759 A | 11/1990 | Kikuchi et al. |
| 4,977,004 A | 12/1990 | Bettle, III et al. |

(Continued)

FOREIGN PATENT DOCUMENTS

CS 111291 6/1964

(Continued)

OTHER PUBLICATIONS

Mehdipour-Ataei, S., et al., "Novel Diols Containing Ester and Amide Groups and Resulting Poly(ester amide ester)s," *J. Applied Polymer Sci.*, 93:2699-2703 (2004), XP002420014.

Database Beilstein [online] Beilstein Institut Zur Förung Der Chemischen Wissenschaften; XP002420038, Beilstein Registry No. 1961007.

Database Caplus [online] Chemical Abstracts Service, Columbus, Ohio, US, XP-002387095, Database Accession No. 1981:572206, Effectiveness of Inhibitors in the Oxidation of Jet Fuel with an Initiator, abstract, Kovalev, et al.

Masada, H. and Oishi, Y., "A New Synthesis of aryl *t*-butyl Ethers," *Chem. Letters*, 57-58 (1978).

(Continued)

*Primary Examiner* — Terressa M Boykin
(74) *Attorney, Agent, or Firm* — Hamilton, Brook, Smith & Reynolds, P.C.

(57) ABSTRACT

Compounds are synthesized that contain nitrogen and hindered phenol functionalities of an aromatic amine and hindered phenol for use as oxidative stabilizers for organic materials, paints, lubricants, elastomers, and in other applications. The disclosed methods can efficiently synthesize target monomers and polymers without the use of expensive catalysts. Further, the disclosed methods can scale up to industrially useful quantities. In general, the methods provide an improved, highly efficient and economical process for the synthesis of macromonomers having nitrogen containing moiety and sterically hindered phenols and their corresponding polymers.

20 Claims, No Drawings

U.S. PATENT DOCUMENTS

| | | | |
|---|---|---|---|
| 4,981,917 A | 1/1991 | MacLeay et al. | |
| 4,994,628 A | 2/1991 | Goddard et al. | |
| 5,013,470 A | 5/1991 | Benfaremo | |
| 5,017,727 A | 5/1991 | Olivier | |
| 5,082,358 A | 1/1992 | Tabata et al. | |
| 5,102,962 A | 4/1992 | Kikuchi et al. | |
| 5,117,063 A | 5/1992 | Stern et al. | |
| 5,143,828 A | 9/1992 | Akkara et al. | |
| 5,185,391 A | 2/1993 | Stokich, Jr. | |
| 5,185,407 A | 2/1993 | Wong | |
| 5,188,953 A | 2/1993 | Johnson et al. | |
| 5,191,008 A | 3/1993 | Frost et al. | |
| 5,196,142 A | 3/1993 | Mollet et al. | |
| 5,206,303 A * | 4/1993 | Tse et al. | 525/319 |
| 5,207,939 A | 5/1993 | Farng et al. | |
| 5,274,060 A | 12/1993 | Schadeli | |
| 5,278,055 A | 1/1994 | Cyrus, Jr. et al. | |
| 5,304,589 A | 4/1994 | Davidson et al. | |
| 5,320,889 A | 6/1994 | Bettle, III | |
| 5,449,715 A | 9/1995 | Plochocka et al. | |
| 5,498,809 A | 3/1996 | Emert et al. | |
| RE35,247 E | 5/1996 | Cyrus, Jr. et al. | |
| 5,516,856 A | 5/1996 | Sanchez | |
| 5,541,091 A | 7/1996 | Wheeler et al. | |
| 5,565,300 A | 10/1996 | Uenishi et al. | |
| 5,574,118 A | 11/1996 | Olivier | |
| 5,652,201 A | 7/1997 | Papay et al. | |
| 5,739,341 A | 4/1998 | Dubs et al. | |
| 5,834,544 A | 11/1998 | Lin et al. | |
| 5,837,798 A | 11/1998 | Hutchings et al. | |
| 5,869,592 A | 2/1999 | Gagne et al. | |
| 5,911,937 A | 6/1999 | Hekal | |
| 5,994,498 A | 11/1999 | Tripathy et al. | |
| 6,018,018 A | 1/2000 | Samuelson et al. | |
| 6,046,263 A | 4/2000 | Rasberger et al. | |
| 6,096,695 A | 8/2000 | Lam et al. | |
| 6,096,859 A | 8/2000 | Akkara et al. | |
| 6,150,491 A | 11/2000 | Akkara | |
| 6,232,314 B1 | 5/2001 | Jarrott et al. | |
| 6,342,549 B1 | 1/2002 | Hirose et al. | |
| 6,444,450 B2 | 9/2002 | Akkara et al. | |
| 6,646,035 B2 | 11/2003 | Koch et al. | |
| 6,723,815 B2 | 4/2004 | Callaghan et al. | |
| 6,743,525 B2 | 6/2004 | Bernsten et al. | |
| 6,770,785 B1 | 8/2004 | Desai et al. | |
| 6,794,480 B2 | 9/2004 | Goto et al. | |
| 6,800,228 B1 | 10/2004 | Semen | |
| 6,828,364 B2 | 12/2004 | Gugumus | |
| 7,132,496 B2 | 11/2006 | Kerres et al. | |
| 7,169,844 B2 | 1/2007 | Inokami | |
| 7,205,350 B2 | 4/2007 | Thibaut | |
| 7,223,432 B2 | 5/2007 | Cholli et al. | |
| 7,262,319 B2 | 8/2007 | Rehm et al. | |
| 7,705,176 B2 | 4/2010 | Cholli et al. | |
| 2001/0041203 A1 | 11/2001 | Uno et al. | |
| 2002/0007020 A1 | 1/2002 | Higashimura et al. | |
| 2002/0128493 A1 | 9/2002 | Romanczyk, Jr. et al. | |
| 2002/0143025 A1 | 10/2002 | Pratt et al. | |
| 2002/0183470 A1 | 12/2002 | Tripathy et al. | |
| 2003/0030033 A1 | 2/2003 | Duyck et al. | |
| 2003/0078346 A1 | 4/2003 | Nakamura et al. | |
| 2003/0091837 A1 | 5/2003 | Aoki | |
| 2003/0176233 A1 | 9/2003 | Romanczyk, Jr. et al. | |
| 2003/0191242 A1 | 10/2003 | Zedda et al. | |
| 2003/0229196 A1 | 12/2003 | Braat et al. | |
| 2003/0230743 A1 | 12/2003 | Cholli et al. | |
| 2004/0015021 A1 | 1/2004 | Adams et al. | |
| 2004/0164279 A1 | 8/2004 | Stevenson et al. | |
| 2004/0180994 A1 | 9/2004 | Pearson et al. | |
| 2004/0186167 A1 | 9/2004 | Dou et al. | |
| 2004/0186214 A1 | 9/2004 | Li et al. | |
| 2004/0198875 A1 | 10/2004 | Kaprinidis et al. | |
| 2004/0214935 A1 | 10/2004 | Cholli et al. | |
| 2005/0170978 A1 | 8/2005 | Migdal et al. | |
| 2005/0209379 A1 | 9/2005 | Botkin et al. | |
| 2005/0238789 A1 | 10/2005 | Cholli et al. | |
| 2005/0242328 A1 | 11/2005 | Baranski | |
| 2006/0029706 A1 | 2/2006 | Cholli et al. | |
| 2006/0040833 A1 | 2/2006 | Al-Akhdar et al. | |
| 2006/0041087 A1 | 2/2006 | Cholli | |
| 2006/0041094 A1 | 2/2006 | Cholli | |
| 2006/0128929 A1 * | 6/2006 | Yang et al. | 528/86 |
| 2006/0128930 A1 * | 6/2006 | Dhawan et al. | 528/86 |
| 2006/0128931 A1 | 6/2006 | Kumar et al. | |
| 2006/0128939 A1 * | 6/2006 | Kumar et al. | 528/373 |
| 2006/0154818 A1 | 7/2006 | Destro et al. | |
| 2006/0189820 A1 | 8/2006 | Rehm et al. | |
| 2006/0189824 A1 | 8/2006 | Kumar et al. | |
| 2006/0208227 A1 | 9/2006 | Shiraki | |
| 2006/0233741 A1 | 10/2006 | Kumar et al. | |
| 2007/0010632 A1 | 1/2007 | Kaplan et al. | |
| 2007/0106059 A1 | 5/2007 | Cholli et al. | |
| 2007/0135539 A1 | 6/2007 | Cholli et al. | |
| 2007/0149660 A1 | 6/2007 | Kumar et al. | |
| 2007/0154430 A1 | 7/2007 | Cholli et al. | |
| 2007/0154608 A1 | 7/2007 | Cholli et al. | |
| 2007/0154720 A1 | 7/2007 | Cholli et al. | |
| 2007/0161522 A1 | 7/2007 | Cholli et al. | |
| 2008/0249335 A1 | 10/2008 | Cholli et al. | |
| 2008/0293856 A1 | 11/2008 | Kumar et al. | |
| 2008/0311065 A1 | 12/2008 | Cholli | |
| 2009/0184294 A1 | 7/2009 | Cholli et al. | |

FOREIGN PATENT DOCUMENTS

| | | | |
|---|---|---|---|
| DE | 197 47 644 A1 | | 5/1999 |
| DE | 198 43 875 A1 | | 3/2000 |
| DE | 19843875 | * | 3/2000 |
| EP | 0 181 023 A1 | | 5/1986 |
| EP | 0 289 077 A2 | | 11/1988 |
| EP | 0 358 157 A1 | | 3/1990 |
| EP | 0 404 039 A1 | | 12/1990 |
| EP | 0 618 203 A1 | | 10/1994 |
| EP | 0 688 805 A1 | | 12/1995 |
| EP | 1 067 144 A1 | | 1/2001 |
| EP | 1468968 | * | 10/2004 |
| FR | 2 183 973 | | 12/1973 |
| GB | 1 283 103 | | 7/1972 |
| GB | 1 320 169 | | 6/1973 |
| GB | 1 372 042 | | 10/1974 |
| GB | 1 389 442 | | 4/1975 |
| GB | 1 469 245 | | 4/1977 |
| GB | 1 482 649 | | 8/1977 |
| JP | 69002715 | * | 1/1966 |
| JP | 69002715 B | | 1/1966 |
| JP | 43016392 | * | 7/1968 |
| JP | 43016392 B4 | | 7/1968 |
| JP | 44024274 | | 10/1969 |
| JP | 44028850 | | 11/1969 |
| JP | 45 2980 | | 1/1970 |
| JP | 49 29339 | | 3/1974 |
| JP | 57085366 A | | 5/1982 |
| JP | 59025814 | | 2/1984 |
| JP | 59197447 | | 11/1984 |
| JP | 60-199832 | | 10/1985 |
| JP | 05 199858 | | 8/1993 |
| JP | 06135876 A | | 5/1994 |
| JP | 06 247959 | | 9/1994 |
| JP | 08027226 A | | 1/1996 |
| JP | 09262069 | | 10/1997 |
| JP | 09 328519 | | 12/1997 |
| JP | 09 328521 | | 12/1997 |
| JP | 9322784 A | | 12/1997 |
| JP | 11-80063 | | 3/1999 |
| JP | 11-158103 | | 6/1999 |
| JP | 2003138258 | | 5/2003 |
| NL | 7 905 000 | | 3/1980 |
| WO | WO 92/20734 | | 11/1992 |
| WO | WO 00/39064 A1 | | 7/2000 |
| WO | WO 01/18125 A1 | | 3/2001 |
| WO | WO 01/48057 A1 | | 7/2001 |
| WO | WO 02/079130 A1 | | 10/2002 |
| WO | WO 03/087260 A1 | | 10/2003 |
| WO | WO 03/102004 A1 | | 12/2003 |
| WO | WO 2004/024070 A2 | | 3/2004 |
| WO | WO 2004/050795 A2 | | 6/2004 |
| WO | WO 2005/025513 A2 | | 3/2005 |
| WO | WO 2005/025646 A2 | | 3/2005 |

| | | | |
|---|---|---|---|
| WO | WO 2005/060500 A2 | 7/2005 | |
| WO | WO 2005/070974 A2 | 8/2005 | |
| WO | WO 2005/071005 A1 | 8/2005 | |
| WO | WO 2006/018403 A1 | 2/2006 | |
| WO | WO 2006/060801 A2 | 6/2006 | |
| WO | WO 2006/104957 A2 | 10/2006 | |
| WO | WO 2008/005358 | 1/2008 | |

OTHER PUBLICATIONS

Ol'dekop, Yu. A., et al. "Simple Synthesis of the tert-butyl Ether of Phenol" Inst. Fiz-Org. Khim., Minsk, USSR. *Zhurnal Obshchei Khimii*, 50(2):475-6 (1980).

Masada, H., et al., "A New Method for the Williamson Ether Synthesis Using *t*-alkyl Halides in Nonpolar Solvents," *The Chemical Society of Japan*, 2:164-166 (1995).

Masada, H. et al., "A New Heterogeneous Williamson Synthesis of Ethers Using *t*-alkyl Substrates," *The Chemical Society of Japan* 3:275-282 (1996).

Tsvetkov, O.N., et al., "Alkylation of Phenols with Higher Olefins. Part I," *Int. Chem. Eng.* 7(1):104-121 (1967).

English Abstract of Kovalev, G. I., et al., "Study of the Effectiveness of Inhibitors in Oxidation of Jet Fuel in a Closed Volume," *Deposited Doc.*, VINITI: 443-82 (1981).

English Abstract of Kovalev, G.I., et al., "Effectiveness of Inhibitors in the Oxidation of Jet Fuel With an Initiator," *J. Neftekhimiya (Petroleum Chemistry)*, 21(2): 287-298 (1981).

Ding, et al., "Chemical Trapping Experiments Support a Cation-Radical Mechanism for the Oxidative Polymerization of Aniline," *Journal of Polymer Science: Part A: Polymer Chemistry*, 37:2569-2579 (1999).

Ciric-Marjanovic, et al., "Chemical Oxidative Polymerization of Aminodiphenylamines," *Journal of Physical Chemistry B*, 112(23): 6976-6987 (2008).

Li, et al., "Novel Multifunctional Polymers," *Chemical Reviews*, 102(9): 2925-2943 (2002).

Translation of Nakatsuka et al. (JP 45-2980), Schreiber Translation, Inc., Jul. 2009.

Hatayama, K., et al., "Anti-ulcer Effect of Isoprenyl Flavonoids. III.[1]) Synthesis and Anti-ulcer Activity of Metabolites of 2'-Carboxymethoxly-4,4'-bis(3-methyl-2-butenyloxy)chalcone[2)]," *Chemical & Pharmaceutical Bulletin*, 33(4), 1327-1333(Apr. 1985).

Spano, R., et al., "Substituted Anilides of 3-Monoethyl Ester of 4-Hydroxyisophthalic Acid," *Journal of Medicinal Chemistry*, 15(5), 552-553 (1987).

Scharpe, S.L., et al., "Serine Peptidase Modulators, Their Preparation, and Their Therapeutic Use," Chemical Abstracts Service, ZCAPLUS, document No. 131:223514 (1999).

Maki, M., et al., "Weather-Resistant Colored Polypropylene," Chemical Abstracts Service, ZCAPLUS, document No. 89:111364 (1978).

Hofer, K., et al., "[[(Anilinooxalyl)amino]phenyl] Phosphite Stabilizers for Polypropylene," Chemical Abstracts Service, ZCAPLUS, document No. 77:62780 (1972).

Thompson, C.R., et al., "Stability of Carotene in Alfalfa Meal: Effect of Antioxidants," *Industrial and Engineering Chemistry*, Western Regional Research Laboratory, Albany, Calif., 42(5); 922-925 (May 1950).

Dordick, J.S., et al., "Polymerization of Phenols Catalyzed by Peroxidase in Nonaqueous Media," *Biotechnology and Bioengineering*, XXX:31-36 (1987).

Kazandjian, R.Z., et al., "Enzymatic Analyses in Organic Solvents," *Biotechnology and* Bioengineering, XXVIII:417-421 (1986).

Klibanov, A.M., et al., "Enzymatic Removal of Toxic Phenols and Anilines from Waste Waters," *J. of Applied Biochemistry*, 2(5):414-421 (1980).

Ikeda, R., et al., "Novel Synthetic Pathway to a Poly(phenylene oxide). Laccase-Catalyzed Oxidative Polymerization of Syringic Acid," *Macromolecules*, 29:3053-3054 (1996).

Akkara, J.A., et al., "Synthesis and Characterization of Polymers Produced by Horseradish Peroxidase in Dioxane," *J. of Polymer Science: Part A: Polymer Chemistry*, 29(11):1561-1574 (1991).

Ayyagari, M.S., et al., "Controlled Free-Radical Polymerization of Phenol Derivatives by Enzyme-Catalyzed Reactions in Organic Solvents," *Macromolecules*, 28(15):5192-5197 (1995).

Ryu, K., et al., "Peroxidase-Catalyzed Polymerization of Phenols," Biocatalysis in Agricultural Biotechnology, Chapter10:141-157 (1988).

Bruno, F.F., et al., "Enzymatic Template Synthesis of Polyphenol," Materials Research Society Symposium Proceedings vol. 600, Electroactive Polymers (EAP):255-259 (1999).

Akkara, J.A., et al., "Hematin-Catalyzed Polymerization of Phenol Compounds," Macromolecules, 33(7):2377-2382 (2000).

Dordick, J.S., "Enzymatic Catalysis in Monophasic Organic Dolvents," *Enzyme Microb. Technol.*, 11(4): 194-211 (1989).

FS&T 821 "Food Lipids," [online], Oct. 2001 [retrieved on Oct. 29, 2002]. Retrieved from the Internet <URL: http://class.fst.ohio-state.edu/fst821/>.

FST 821 "Course Schedule," [online], [retrieved on Oct. 29, 2002]. Retrieved from the Internet <URL: http://class.fst.ohio-state.edu/fst821/>.

FS&T 821 "Antioxidant," [online], [retrieved on Oct. 29, 2002]. Retrieved from the Internet <URL: http://class.fst.ohio-state.edu/fst821/>.

Jialanella, G.and Pilrma, I., "Synthesis of Poly(vinyl alcohol-co-vinyl gallate) by the Chemical Modification of Poly(vinyl alcohol)," Polymer Bulletin 18:385-389 (1987).

Jayaprakasha, G.K., et al., "Antioxidant Activity of Grape Seed (*Vitis vinifera*) Extracts on Peroxidation Models in Vitro," *Food Chemistry*, 73:285-290 (2001).

Hidalgo, M.E., et al., "Antioxidant Activity of Depsides and Depsidones," Phytochemistry, 37(6):1585-1587 (1994).

Khan, K.M., et al., "An Expedient Esterification of Aromatic Carboxylic Acids Using Sodium Bromate and Sodium Hydrogen Sulfite," *Tetrahedron* 59(29):5549-5554 (2003).

March, J., Advanced Organic Chemistry, McGraw Hill Book Company, New York, pp. 251-259 (1977).

Mehdipour-Ataei, S., et al., "Novel Diols Containing Ester and Amide Groups and Resulting Poly(ester amide ester)s," *J. Applied Polymer Sci.*, 93:2699-2703 (2004), XP002420014.

Masada, H. and Oishi, Y., "A New Synthesis of aryl *t*-butyl Ethers," *Chem. Letters*, 57-58 (1978).

Ol'dekop, Yu. A., et al. "Simple Synthesis of the tert-butyl Ether of Phenol" Inst. Fiz-Org. Khim., Minsk, USSR. *Zhurnal Obshchei Khimii*, 50(2):475-6 (1980).

Masada, H., et al., "A New Method for the Williamson Ether Synthesis Using *t*-alkyl Halides in Nonpolar Solvents," *The Chemical Society of Japan*, 2:164-166 (1995).

Masada, H. et al., "A New Heterogeneous Williamson Synthesis of Ethers Using *t*-alkyl Substrates," *The Chemical Society of Japan* 3:275-282 (1996).

Tsvetkov, O.N., et al., "Alkylation of Phenols with Higher Olefins. Part I," *Int. Chem. Eng.* 7(1):104-121 (1967).

Sartori G., et al., "Highly Selective Mono-*tert*-butylation of Aromatic Compounds," *Chem. Ind.*, (London), (22):762-763 (1985).

Koshchii, V.A., et al. "Alkylation of Phenol by Alcohols in the Presence of Alumium Phenolate," *Org. Chem.* 24(7): 1358-1361 (1988).

Chandra, K.G. and Sharma, M.M., "Alkylation of Phenol with MTBE and Other tert-butylethers:Cation Exchange Resins as Catalysts," *Catal. Lett.* 19(4):309-317 (1993).

Sakthivel, A., et al., "Vapour Phase Tertiary Butylation of Phenol Over Sulfated Zirconia Catalyst," *Catal. Lett.*, 72(3-4):225-228 (2001).

Quaschning, V., et al., "Properties of Modified Zirconia Used as Friedel-Crafts-Acylation Catalysts," *J. Catal.* 177:164-174 (1998).

Badamali, S.K., et al., "Influence of Aluminium Sources on the Synthesis and Catalytic Activity of Mesoporous AIMCM-41 Molecular Sieves," *Catal. Today* 63:291-295 (2000).

Heidekum, A., et al., "Nafion/Silica Composite Material Reveals High Catalytic Potential in Acylation Reactions," *J. Catal.* 188:230-232 (1999).

Kamitori, Y., et al., "Silica Gel as an Effective Catalyst for the Alkylation of Phenols and Some Heterocylic Aromatic Compounds," *J. Org. Chem.* 49: 4161-4165 (1984).

Armengol, E., et al., "Acid Zeolites as Catalysts in Organic Reactions, *tert*-Butylation of Anthracene, Naphthalene and Thianthrene," *Appl. Catal. A* 149:411-423 (1997).

Lalancette, J.M., et al.,, "Metals Intercalated in Graphite. II. The Friedel-Crafts Reactions with ALCL$_3$-Graphite," *Can. J. Chem.* 52:589-591 (1974).

Overgaag, M., et al., "Rearrangement of Alkyl Phenyl Ethers Over Dealuminated HY Zeolites Under Liquid-Phase Conditions," *Applied Catalysis A: General, Elsevier Sci.*, 175(1-2):139-146 (1998).

Devassy, B.M., et al., "Zirconia Supported Phosphotungstic Acid as an Efficient Catalyst for Resorcinol *tert*-Butylation and *n*-Heptane Hydroisomerization," *J. Mol. Catalysis A: Chemical* 221:113-119 (2004).

XP-002419239, "Discover Our World of Effects for Polyolefins," *Ciba Speciality Chemicals*, (2003).

Pirozhenko, V.V., et al., "NMR Study of Topomerization of *N*-Aroyl-*p*-Benzoquinonemonoimines," *Russian J. of Organic Chem.*, 31(11):1514-1519 (1995).

Coppinger, G.B., et al., "Photo-Fries Rearrangement of Aromatic Esters. Role of Steric and Electronic Factors" *J. of Phy. Chem.*, 70(11):3479-3489 (1966).

Spano, R., et al., "Substituted Anilides of 3-Monoethyl Ester of 4 Hydroxyisophthalic Acid," *J. of Med. Chem.*, 15(5):552-553 (1972).

Mejias, L., et al.,, "New Polymers From Natural Phenols Using Horseradish or Soybean Peroxidase," *Macromol. Biosci.*, 2:24-32 (2002).

Ismail, M.N. And Wazzan, A.A., "Evaluation of New Thermal Stabilizers and Antifatigue Agents for Rubber Vulcanizates," *Polymer-Plastics Tech. and Eng.*, 45:751-758 (2006).

Joossens, J., et al., "Diphenyl Phosphonate Inhibitors for the Urokinase-Type Plasminogen Activator: Optimization of the P4 Position," *J. Med. Chem.*, 49:5785-5793 (2006).

Belyaev, A., et al., "Structure-Activity Relationship of Diaryl Phosphonate Esters as Potent Irreversible Dipeptidyl Peptidase IV Inhibitors," *J. Med. Chem.*, 42:1041-1052 (1999).

Blokhin, Y.I, et al., "Phosphorylation of Dihydric Phenols with Amides of Phosphorous Acid," *Russian Chem. Bulletin*, 45(9):2250-2251 (1996).

Pätoprstý, V., et al., "$^{13}$C NMR Study of 3,9-Di(alkylphenoxy)-2,4,8,10-tetraoxa-3,9-diphosphaspiro[5.5]undecanes," *Magnetic Resonance in Chem*, 23(2):122-126 (1985).

Singh, A. and Kaplan, D. L., "Biocatalytic Route to Ascorbic Acid-Modified Polymers for Free-Radical Scavenging," *Adv. Matter.*, 15(15):1291-1294 (2003).

Kim, T. H., et al., "Melt Free-Radical Grafting of Hindered Phenol Antioxidant onto Polyethylene," *J. Applied Polymer Science*, 77:2968-2973 (2000).

Faber, K., "Biotransformations in Organic Chemistry," A Textbook, Fourth Completely Revised and Extended Edition, Springer-Verlag pp. 347-349 (1953).

Database CA [online] Chemical Abstracts Service, Columbus, Ohio, US, XP-002429584, Database Accession No. 81::153647, Organic Phosphate Stabilizers for Polyamides and Polyurethanes, abstract, Minagawa, M. (1974).

International Search Report for related foreign application PCT/US2007/015177, mailed on Jun. 13, 2008.

International Search Report for related foreign application PCT/US2005/044021, mailed on May 22, 2006.

International Search Report for related foreign application PCT/US2005/044022, mailed on May 2, 2006.

International Search Report for related foreign application PCT/US2005/044023, mailed on Nov. 3, 2006.

International Search Report for related foreign application PCT/US2005/044019, mailed on Apr. 28, 2006.

International Search Report for related foreign application PCT/US2005/025646, mailed on Mar. 13, 2006.

International Search Report for related foreign application PCT/US2005/025513, mailed on Mar. 13, 2006.

International Search Report for related foreign application PCT/US2006/006355, mailed on Jul. 31, 2006.

International Search Report for related foreign application PCT/US2006/010985, mailed on Dec. 19. 2006.

International Search Report for related foreign application PCT/US2006/042240, mailed on May 3, 2007.

International Search Report for related foreign application PCT/US2006/042235, mailed on Apr. 27, 2007.

International Search Report for related foreign application PCT/US2006/045929, mailed on Apr. 20, 2007.

Ismail, M.N. and Wazzan, A.A., "Evaluation of New Thermal Stabilizers and Antifatigue Agents for Rubber Vulcanizates," *Polymer-Plastics Tech. and Eng.*, 45:751-758 (2006).

Masada, H., et al., "A New Method for the Williamson Ether Synthesis Using *t*-alkyl Halides in Nonpolar Solvents," *The Chemical Society of Japan*, 2:164-166 (1995).

Scharpe, S.L., et al., "Serine Peptidase Modulators, Their Preparation, and Their Therapeutic Use," Chemical Abstracts Service, ZCAPLUS, document No. 131:223514 (1999).

Notification of Transmittal of International Search Report and the Written Opinion of the International Searching Authority, or the Declaration in International Application PCT/US2006/042251 mailed Feb. 22, 2007.

Notification Concerning Transmittal of International Preliminary Report on Patentability for related foreign application PCT/US2007/015177, mailed on Jan. 6, 2009.

Al-Malaika, S and Suharty, N., "Reactive Processing of Polymers: Mechanisms of Grafting Reactions of Functional Antioxidants on Polyolefins in the Presence of a Coagent," Polymer Degradation and Stability 49: 77-89 (1995).

Written Opinion for related foreign application PCT/US2005/025646, mailed on Nov. 14, 2006.

International Preliminary Report on Patentability for related foreign application PCT/US2005/025646, mailed on Dec. 12, 2006.

Office Action for related foreign application EP05773305.7 dated Apr. 24, 2008.

Examiner's Report No. 1 for related foreign application AU 2005269754 dated Apr. 1, 2008.

Examiner's Report No. 1 for related foreign application AU 2005269780 dated Apr. 2, 2008.

Examiner's Report No. 2 for related foreign application AU 2005269754 dated Jan. 5, 2010.

Examiner's Report No. 3 for related foreign application AU 2005269754 dated Jan. 12, 2010.

International Preliminary Report on Patentability and Written Opion for related foreign application PCT/US2005/025513, mailed on Jan. 23, 2007.

Office Action for related foreign application EP06720996.5-2103 dated Mar. 23, 2009.

Office Action for related foreign application EP06720996.5-2103 dated Apr. 21, 2008.

RN 85650-63-1, 1984.

International Preliminary Report on Patentability for related foreign application PCT/US2005/001946, dated Jul. 24, 2006.

Notification Concerning Transmittal of International Preliminary Report on Patentability for application PCT/US2006/042251, mailed on May 8, 2008.

Notification of Transmittal of International Search Report and Written Opinion of the International Searching Authority, or the Declaration for Application PCT/US2006/042251, mailed on Feb. 22, 2007.

Notification Concerning Transmittal of International Preliminary Report on Patentability for related foreign application PCT/US2005/025513, dated Feb. 1, 2007.

* cited by examiner

SYNTHESIS OF ANILINE AND PHENOL-BASED ANTIOXIDANT MACROMONOMERS AND CORRESPONDING POLYMERS

RELATED APPLICATION

This application claims the benefit of U.S. Provisional Application No. 60/633,196, filed on Dec. 3, 2004. The entire teachings of the above application(s) are incorporated herein by reference.

BACKGROUND OF THE INVENTION

Sterically hindered 3-hydroxyphenyl propionic acid esters and certain amide derivatives are known to be effective antioxidants for a wide range of organic substrates, particularly lubricants and polymers, protecting them from oxidative and thermal degradation. In general, these are prepared by the transesterification of corresponding carboxylic acid derivatives with various alcohols and amines. Various catalysts for this reaction are known, e.g. acids, bases, amines, metal alkoxides and also organotin compounds. It is economically advantageous if the reaction is carried out in the melt state without using any catalyst, or using a less expensive or improved catalyst. Moreover, it is desirable to have a reaction process in which subsequent steps for separating the desired product from the reaction mixture is not required. In some cases the formation of discolored or stained products resulting from the presence of catalyst residues reaction is extremely undesirable. Certain end product properties, such as stability, or low toxicity, are some times negatively influenced if the trace levels of catalysts are in the final product. Therefore, an alternative process without involving the use of catalysts or using improved catalysts is desirable. In our earlier patent applications, 60/370,468, Ser. Nos. 10/408,679, 10/761,933, PCT/US03/10782, PCT/US2005/001946, 60/590,575, 60/590,646, Ser. No. 11/184,724, PCT/US2005/025646, Ser. No. 11/184,716 and PCT/US2005/025513 the synthesis of poly (sterically hindered phenol) antioxidants was demonstrated from substituted phenols. These macromonomer and polymeric antioxidants showed significantly improved antioxidant activities in cooking oils, plastics, lubricants and other industrial applications compared to currently used (monomeric) antioxidants. However, the synthesis of monomers for these polymers is tedious and requires expensive catalysts.

SUMMARY OF THE INVENTION

The present invention relates to the synthesis of compounds containing nitrogen and hindered phenol functionalities of an aromatic amine and hindered phenol for use as oxidative stabilizers for organic materials, paints, lubricants, elastomers, and in other applications.

Disclosed is a catalyst-free method of preparing a macromonomer represented by Structural Formula I. The method comprises combining sterically hindered phenol IA and aminophenol IB; The method further comprises the step of heating to reflux the combination of sterically hindered phenol IA and aminophenol IB to create a macromonomer represented by Structural Formula I.

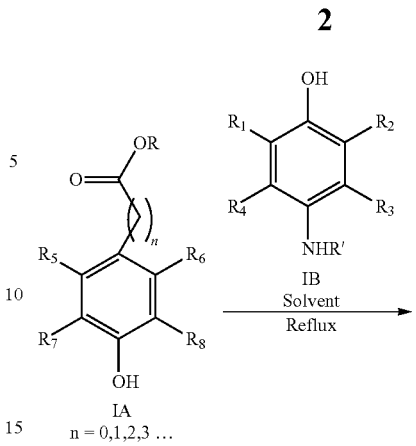

IA
n = 0,1,2,3 ...

IB
Solvent
Reflux

I
n = 0,1,2,3 ...

Each of R and $R_1$-$R_8$ are independently —H, —OH, or a C1-C10 alkyl group. n is an integer from 0 to 24. R' is —H, optionally substituted C1-C20 alkyl or optionally substituted aryl group.

In another embodiment, the present invention is a method for synthesizing an antioxidant polymer represented by Structural Formula IV. The method comprises acetylating a hydroxyl group of a compound represented by Structural Formula IA to create an acetlylated phenol represented by Structural Formula II; combining the acetlylated phenol represented by Structural Formula II and amino phenol represented by Structural Formula IB; heating to reflux the combination acetylated phenol II and aminophenol IB to create a macromonomer represented by Structural Formula III; and polymerizing the macromonomer represented by Structural Formula III using an oxidative polymerization catalyst followed by acidic deacetylation to form the antioxidant polymer represented by Structural Formula IV:

IA
$\xrightarrow{Ac_2O, acid}$

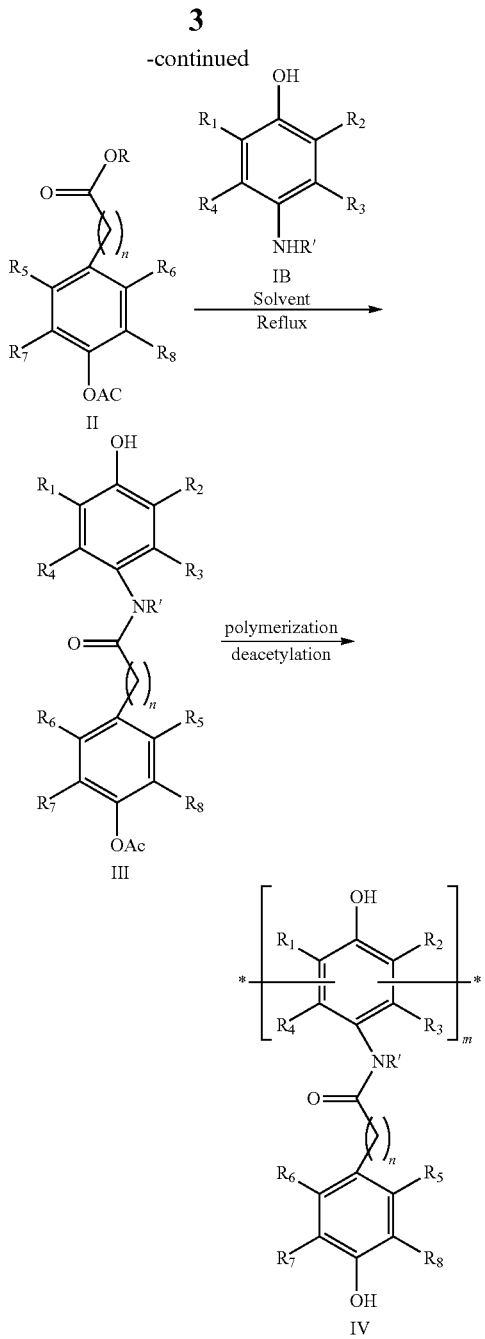

Each of R, and $R_1$-$R_8$ are independently —H, —OH, or a C1-C10 alkyl group. n is an integer from 0 to 24. m is an integer equal to 2 or greater. R' is —H, optionally substituted C1-C20 alkyl or optionally substituted aryl group.

In another embodiment, the present invention is a method of preparing a macromonomer represented by Structural Formula I using a catalyst selected from boric acid, meta boric acid, para-toluene, sulfonic acid, anhydrous sodium acetate, lithium acetate or lithium amide.

The disclosed catalysts are inexpensive, increase the rate of reaction and give a higher yield and better product color as compared to the currently used catalysts. The disclosed methods can efficiently synthesize the target monomers and polymers without the use of expensive catalysts. Further, these methods can scale up to industrially useful quantities. In general, the present invention pertains to an improved, highly efficient and economical process for the synthesis of macromonomers having nitrogen containing moiety and sterically hindered phenols and their corresponding polymers.

DETAILED DESCRIPTION OF THE INVENTION

A description of preferred embodiments of the invention follows.

The present invention relates to the synthesis of compounds containing nitrogen and hindered phenol functionalities of an aromatic amine and hindered phenol that could act as an oxidative stabilizer for organic materials, paints, lubricants, elastomers, and in other applications. In particular, the present invention pertains to an improved, highly efficient and economical process for the synthesis of macromonomers having nitrogen containing moiety and sterically hindered phenols and their corresponding polymers.

The present invention is generally directed to methods of synthesizing monomers for (sterically hindered phenol) antioxidant polymers. Such antioxidants can be employed to inhibit the oxidation of an oxidizable material, for example by contacting the material with an antioxidant polymer made by the methods of the present invention.

Sterically hindered, as used herein means that the substituent group (e.g., bulky alkyl group) on a ring carbon atom adjacent (or para) to a ring carbon atom substituted with a hydroxy group (or thiol or amine group), is large enough to sterically hinder the hydroxy group (or thiol or amine groups). This steric hindrance, in certain embodiments results in more labile or weak bonding between the oxygen and the hydrogen (or sulfur or nitrogen and hydrogen) and in turn enhances the stability and antioxidant activity (proton donating activity) of the sterically hindered antioxidant.

Such antioxidant polymers can be employed to inhibit the oxidation of an oxidizable material, for example by contacting the material with an antioxidant polymer made by the methods of the present invention.

For purposes of the present invention, a method of "inhibiting oxidation" is a method that inhibits the propagation of a free radical-mediated process. Free radicals can be generated by heat, light, ionizing radiation, metal ions and some proteins and enzymes. Inhibiting oxidation also includes inhibiting reactions caused by the presence of oxygen, ozone or another compound capable of generating these gases or reactive equivalents of these gases.

As used herein the term "oxidizable material" is any material which is subject to oxidation by free-radicals or oxidative reaction caused by the presence of oxygen, ozone or another compound capable of generating these gases or reactive equivalents thereof. In particular the oxidizable material is a lubricant or a mixture of lubricants.

Repeat units of the antioxidant polymers of the invention include substituted benzene molecules. These benzene molecules are typically based on phenol or a phenol derivative, such that they have at least one hydroxyl or ether functional group. Preferably, the benzene molecules have a hydroxyl group. The hydroxyl group can be a free hydroxyl group and can be protected or have a cleavable group attached to it (e.g., an ester group). Such cleavable groups can be released under certain conditions (e.g., changes in pH), with a desired shelf life or with a time-controlled release (e.g., measured by the half-life), which allows one to control where and/or when an antioxidant polymer can exert its antioxidant effect. The repeat units can also include analogous thiophenol and aniline derivatives, e.g., where the phenol —OH can be replaced by —SH, —NH—, and the like.

Substituted benzene repeat units of an antioxidant polymer of the invention are also typically substituted with a bulky alkyl group or an n-alkoxycarbonyl group. Preferably, the benzene monomers are substituted with a bulky alkyl group. More preferably, the bulky alkyl group is located ortho or meta to a hydroxyl group on the benzene ring, typically ortho. A "bulky alkyl group" is defined herein as an alkyl group that is branched alpha-or beta-to the benzene ring. Preferably, the alkyl group is branched alpha to the benzene ring. More preferably, the alkyl group is branched twice alpha to the benzene ring, such as in a tert-butyl group. Other examples of bulky alkyl groups include isopropyl, 2-butyl, 3-pentyl, 1,1-dimethylpropyl, 1-ethyl-1-methylpropyl and 1,1-diethylpropyl. The bulky alkyl groups are preferably unsubstituted, but they can be substituted with a functional group that does not interfere with the antioxidant activity of the molecule or the polymer. Straight chained alkoxylcarbonyl groups include methoxycarbonyl, ethoxycarbonyl, n-propoxycarbonyl, n-butoxycarbonyl and n-pentoxycarbonyl. n-propoxycarbonyl is a preferred group. Similar to the bulky alkyl groups, n-alkoxycarbonyl groups are optionally substituted with a functional group that does not interfere with the antioxidant activity of the molecule or the polymer.

In one embodiment the present invention is a catalyst-free method of preparing a macromonomer represented by Structural Formula I' (or I). The method comprises a step of mixing sterically hindered monomer IA' (or IA) and aminophenol IB' (or IB) in a suitable solvent and heating the reaction mixture to reflux as shown in Scheme 1.

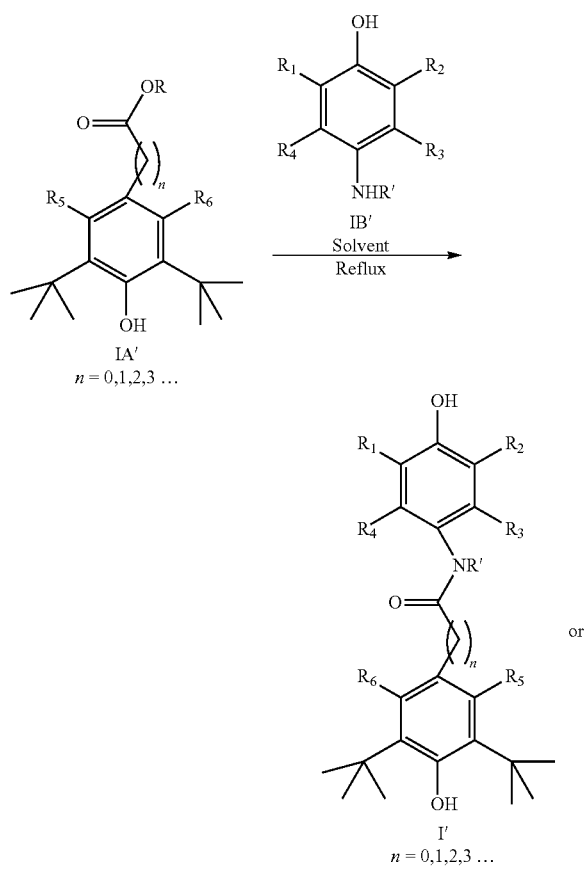

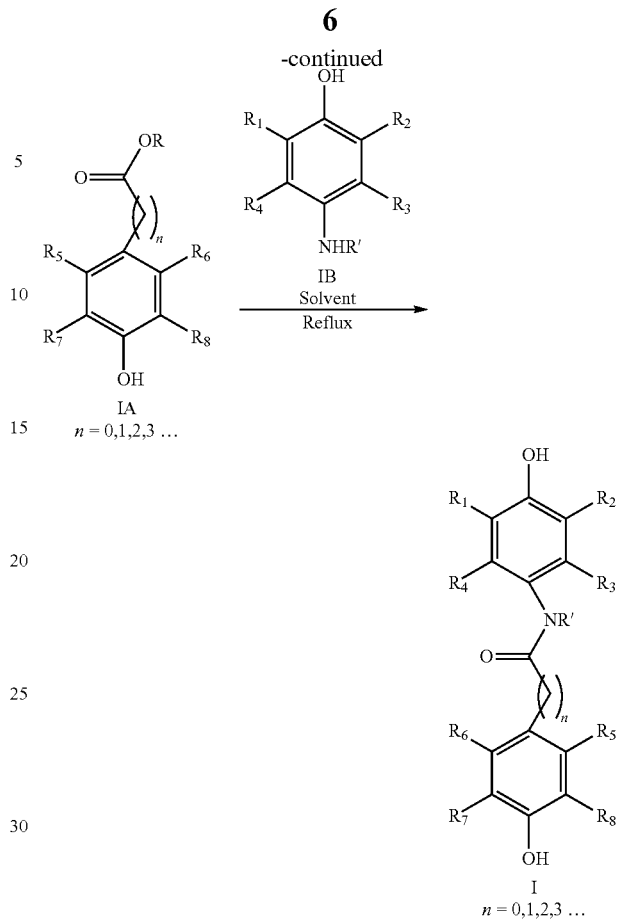

In Scheme 1, R and $R_1$-$R_6$ are independently —H, —OH, or a C1-C10 alkyl group. In one embodiment, $R_1$-$R_6$ are independently be —OH or —H. Additional values for $R_1$-$R_6$ independently an optionally substituted aryl group, and optionally substituted alkoxy group, an optionally substituted carbonyl group, an optionally substituted alkoxycarbonyl group, an optionally substituted aryloxycarbonyl group, —SH or —$NH_2$. n is an integer from 0 to 24. $R_7$-$R_8$ are independently —H, —OH, or a C1-C10 alkyl group. Additional values for $R_7$-$R_8$ independently an optionally substituted aryl group, and optionally substituted alkoxy group, an optionally substituted carbonyl group, an optionally substituted alkoxycarbonyl group, an optionally substituted aryloxycarbonyl group, —SH or —$NH_2$. Preferably, $R_7$-$R_8$ are C1-C10 alkyl groups. More preferably, $R_7$-$R_8$ are independently methyl or tert-butyl groups. Even more preferably $R_7$-$R_8$ are tert-butyl groups. R' is —H, optionally substituted C1-C20 alkyl or optionally substituted aryl group. In certain embodiments R' is —H or a C1-C10 alkyl group. Preferably R' is —H.

The method comprises a step of mixing sterically hindered monomer IA' (or IA) and aminophenol IB' (or IB) in a suitable solvent and heating the reaction mixture and optionally refluxing as shown in Scheme I.

The reaction mixture is heated to between 30 and 150° C., between 50 and 120° C., between 80 and 110° C., The one-pot process for the synthesis of macromonomer I' (or I) does not require any catalyst and can simply made by mixing the two components in a suitable solvent and heating the reaction mixture optionally to reflux as shown in Scheme 1.

As used herein a one pot process can involve one or more steps, however, the products of each step do not have to be isolated or purified between steps and all of the steps can take place on one container.

The one pot synthetic process involves the mixing of sterically hindered phenolic acid derivatives, preferably 3-(3,5-di-tertbutyl, 4-hydroxyphenyl)propionic acid, 3,5-di-tertbutyl, 4-hydroxybenzoic acid or their lower alkyl esters with substituted amino phenols most preferably 4-amino phenol in a suitable solvent. The solvent used in the this process may be one or mixture solvents. The prefered solvent for the process is a mixture of toluene and N-methylpyrrolidone (NMP) in a prefered ratio of 10:1. The prefered method of this disclosure is the mixing of equimoles of 3-(3,5-di-tertbutyl, 4-hydroxyphenyl)propionic acid and 4-amino phenol in a 10:1 mixture of toluene and NMP and optionally refluxing the reaction mixture at 100° C. using a Dean's Stark apparatus to remove the water that is produced in the reaction. The process is very simple and highly efficient, economical and do not require any catalyst.

In certain embodiments, the methods of the present invention for the synthesis of polymer of Structure IV' (or (IV)) is a four step process. In the first step sterically hindered phenolic acid derivatives, prefebly 3-(3,5-di-tertbutyl, 4-hydroxyphenyl)propionic acid, 3,5-di-tertbutyl, 4-hydroxybenzoic acid or their lower alkyl esters are acetylated to their phenolic acetates of Structure II' (or (II)), with acetic anhydride by acid catalysis. In the second step the phenolic acetate II' (or (II)) is reacted with an amino phenol (for example, refluxing in a 10:1 mixture of toluene and NMP) to give an acetylated macromonomer of Structure III' (or (III)). The third step is polymerization (using biocatalysts horse radish peroxidase, or biomimetic catalysts such as Hematin, inorganic catalysts such as Fe-salen, or other catalysts) of the macromonomer to produce a polymer, The fourth step is deacetylation of to produce the polymer represented by Structural Formula IV' (or (IV)).

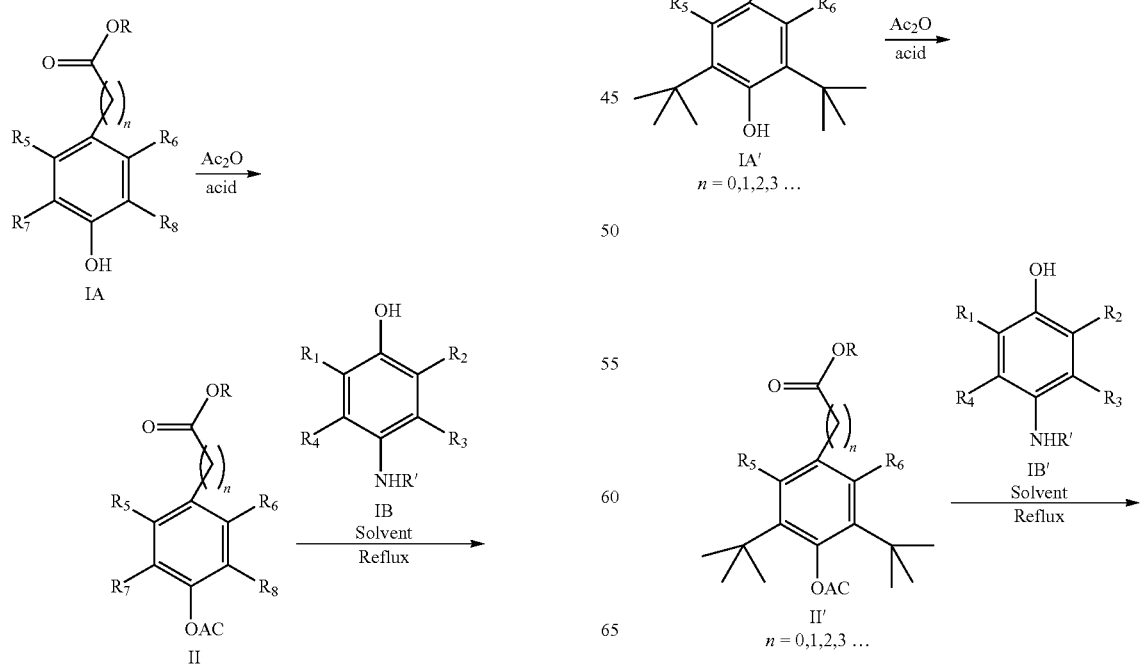

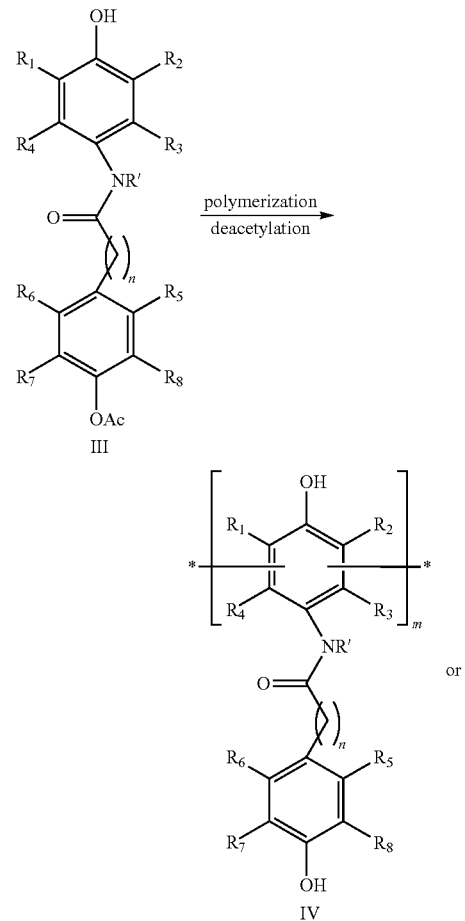

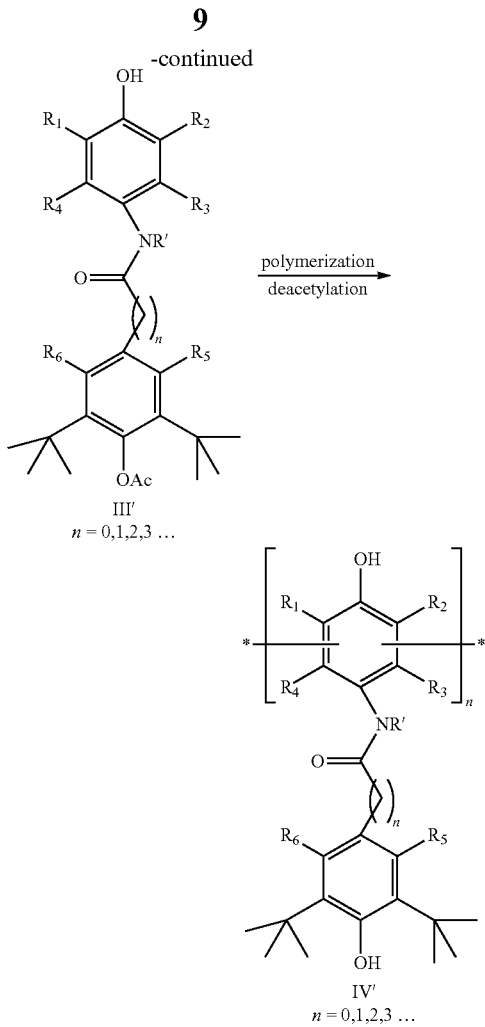

The variables and preferred variables are as described above for Scheme 1.

In certain embodiments, in the first step the sterically hindered phenol acid is acetylated to give a phenolic acetate. The reaction comprises reacting the sterically hindered phenolic acid with an acetic anhydride under acid conditions. As used herein under acidic conditions means that the reaction is carried out in the presence of an acid or an acid catalyst, for example, concentrated sulfuric acid and p-tolunene sulfonic acid.

In certain embodiments, the acetylation reaction is performed at room temperature (between 20 and 28° C.). In certain embodiments the sterically hindered phenol acid is dissolved in acetic anhydride and a small amount of catalyst is added. In certain embodiment, the reaction is carried out between 1 and 24 hrs, between 2 and 12 hours between 6 and 8 hrs. In certain embodiments the reaction is monitored by thin-layer chromatography.

In certain embodiments the second step comprises reacting the phenolic acetate with an amino phenol to give the macromonomer represented by III' (or (III)). The reaction is carried out optionally under reflux conditions. The reaction mixture of phenolic acetate with an amino phenol is heated to between 30 and 150° C., between 50 and 120° C., between 80 and 110° C., The one-pot process for the synthesis of macromonomer III' (or (III) does not require any catalyst and can simply made by mixing the two components in a suitable solvent and heating the reaction mixture to reflux as shown in Scheme 1 and Scheme 2.

The one pot synthetic process involves the mixing of sterically hindered phenolic acetate derivatives with substituted amino phenols most preferably 4-amino phenol in a suitable solvent. The solvent used in this process may be one or a mixture of solvents. The prefered solvent for the process is a mixture of toluene and N-methylpyrrolidone (NMP) in a prefered ratio of 10:1. The prefered method of this disclosure is the mixing of equimoles of 3-(3,5-di-tertbutyl, 4-hydroxyphenyl)propionic acid and 4-amino phenol in a 10:1 mixture of toluene and NMP and typically refluxing the reaction mixture at 100° C. using a Dean's Stark apparatus to remove the water that is produced in the reaction. The process is very simple and highly efficient, economical and do not require any catalyst. In certain embodiment the solvents used can be, for example, xylene, dichlorobenzene, or a combination thereof.

In another embodiment, the third step is a method for polymerizing an acetylated macromonomer represented by Structural Formula III' (or (III)). In certain embodiments the method of polymerization comprises using an oxidative polymerization catalyst.

In certain embodiment an oxidative polymerization catalyst along with an oxidant, e.g., hydrogen peroxide or organic peroxide is used to polymerize the monomers made by the methods of the present invention. As used herein the oxidant serves as a substrate for the catalyst. The oxidative polymerization catalyst and oxidant combined facilitate the oxidation of the monomer to form a polymer.

An oxidative polymerization catalyst is added along with an oxidant, e.g., hydrogen peroxide or organic peroxide to convert the monomer to a polymer.

As used herein the oxidant serves as a substrate for the catalyst. The oxidative polymerization catalyst and oxidant combined facilitate the oxidation of the monomer to form a polymer.

Polymerization of the monomers can be catalyzed by a natural or synthetic enzyme or an enzyme mimetic capable of polymerizing a substituted benzene compound in the presence of hydrogen peroxide, where the enzyme or enzyme mimetic typically have a heme or related group at the active site. One general class of enzymes capable of catalyzing this reaction can be commonly referred to as the peroxidases. Horseradish peroxidase, soybean peroxidase, *Coprinus cinereus* peroxidase, and *Arthromyces ramosus* peroxidase are readily available peroxidases. Other enzymes capable of catalyzing the reaction include laccase, tyrosinase, and lipases. Suitable enzymes are able to catalyze the formation of a carbon-carbon bond and/or a carbon-oxygen-carbon bond between two aryl (e.g., phenyl, phenol) groups when a peroxide (e.g., hydrogen peroxide or an organic peroxide) can be present. A subunit or other portion of a peroxidase can be acceptable, provided that the active site of the enzyme can be still functional. Enzyme mimetics typically correspond to a part of an enzyme, so that they can carry out the same reaction as the parent enzyme but are generally smaller than the parent enzyme. Also, enzyme mimetics can be designed to be more robust than the parent enzyme, such as to be functional under a wider variety of conditions (e.g., different pH range, aqueous, partially aqueous and non-aqueous solvents) and less subject to degradation or inactivation. Suitable enzyme mimetics include hematin, tyrosinase-model complexes and iron-salen complexes. Hematin, in particular, can be functionalized to allow it to be soluble under a wider variety of conditions is disclosed in U.S. application Ser. No. 09/994, 998, filed Nov. 27, 2001, the entire teachings of which are incorporated herein by reference.

Polymerizations of the present invention can be carried out under a wide variety of conditions. The pH can be often between about pH 1.0 and about pH 12.0, typically between about pH 6.0 and about pH 11.0. The temperature can be above about 0° C., such as between about 0° C. and about 100° C., 0° C. and about 45° C. or between about 15° C. and about 30° C. (e.g., room temperature). The solvent can be aqueous (preferably buffered), organic, or a combination thereof. Organic solvents are typically polar solvents such as ethanol, methanol, isopropanol, dimethylformamide, dioxane, acetonitrile, and diethyl ether. The concentration of monomer or comonomers can be typically 0.001 M or greater. Also, the concentration of buffer can be typically 0.001 M or greater.

Polymerizations of the invention use a catalytic amount of one of the enzymes or enzyme mimetics described above, which can be between about one unit/mL and five units/mL, where one unit can form 1.0 mg purpurogallin from pyrogallol in 20 seconds at pH 6.0 at 20° C. Preferably, the enzyme or enzyme mimetic can be added to the solution after addition of the antioxidant monomer or comonomers. A peroxide can be then added incrementally to the reaction mixture, such as not to de-activate the enzyme or enzyme mimetic, until an amount approximately stoichiometric with the amount of antioxidant monomer or comonomers has been added.

Although the enzyme or enzyme mimetic can be responsible for formation of phenol-based free radicals needed for chain propagation, the coupling of radicals to form a polymer chain can be controlled by the phenoxy radical and solvent chemistries. Further details regarding the coupling of phenoxy radicals can be found in "Enzymatic catalysis in monophasic organic solvents," Dordick, J. S., *Enzyme Microb. Technol.* 11:194-211 (1989), the contents of which are incorporated herein by reference. Coupling between substituted benzene monomers typically occurs ortho and/or para to a hydroxyl group. Coupling rarely occurs meta to a hydroxyl group.

Polymerization preferably results in the formation of C—C bonds. Preferred polymers can contain at least about 95% C—C bonds, at least about 90% C—C bonds, at least about 80% C—C bonds, at least about 70% C—C bonds, at least about 60% C—C bonds or at least about 50% C—C bonds. Especially preferred polymers contain about 100% C—C bonds. The remaining bonds are typically C—O—C bonds.

In certain other embodiments the polymerization is carried out in the presence of an inorganic or organometallic catalyst, such as ferric chloride, ammonium persulphate, Iron(III) chloride, Iron(III) bromide, aluminum chloride, zinc chloride, TEMPO, AIBN, bis(cyclopentadienyl)titanium dichloride, 2.di-alkyl-aluminimum, chloride compounds, 3.triethyl aluminum and titanium tetra chloride, 4.Bis-Cyclopentadienyl, Zirconium Dichloride and 5 Ta(CH-t-Bu)(CH2-t-Bu)$_3$.

In certain other embodiments the polymerization is carried out in the presence of an inorganic or organometallic catalyst, such as ferric chloride, ammonium persulphate, Iron(III) chloride, Iron(III) bromide, aluminum chloride, zinc chloride, TEMPO, AIBN, bis(cyclopentadienyl)titanium dichloride, 2.di-alkyl-aluminimum, chloride compounds, 3.triethyl aluminum and titanium tetra chloride, 4.Bis-Cyclopentadienyl, Zirconium Dichloride and 5 Ta(CH-t-Bu)(CH2-t-Bu)$_3$.

In certain embodiments, the fourth step comprises deacetylation under acidic conditions to produce the polymer of Structure IV.

In one embodiment the present invention is a method of synthesizing a macromonomer represented by:

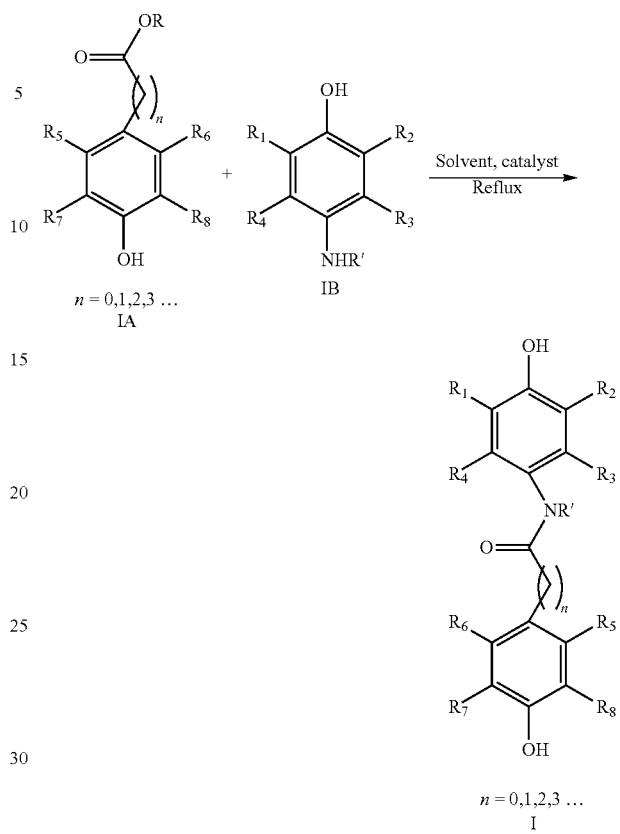

The method comprises mixing sterically hindered phenol IA and aminophenol IB in an organic solvent; or a mixture of organic solvents and heating the reaction mixture to reflux. Each of R and $R_1$-$R_8$ are independently —H, —OH, or a C1-C10 optionally substituted branched or straight chain alkyl group; and n is an integer from 0 to 24. In certain embodiments, at least one of $R_1$-$R_6$ is a tertiary butyl group. In certain other embodiments, $R_7$ and $R_8$ are tertiary butyl group. In certain other embodiments at least one of $R_7$ and $R_8$ is a methyl and the other is a tertiary butyl group. R' is —H, optionally substituted C1-C20 alkyl or optionally substituted aryl group. In certain embodiments R' is —H or a C1-C10 alkyl group. Preferably R' is —H.

The reaction conditions are as described above for Scheme 1.

In another embodiment, the present invention is a method of synthesizing a macromonomer represented by Structural Formula I, comprising the steps of:

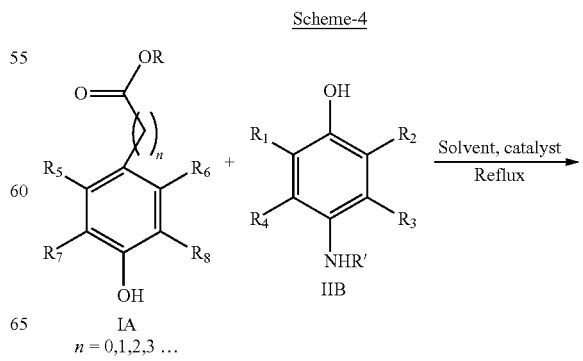

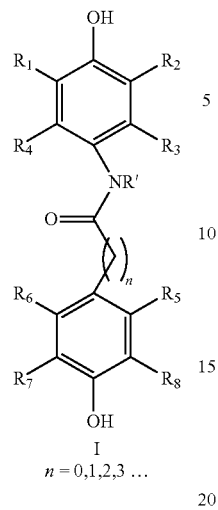

I
n = 0,1,2,3 ...

mixing sterically hindered phenol IA and aminophenol IB in an organic solvent; or a mixture of organic solvents and heating the reaction mixture to reflux in the presence of a catalyst.

In certain embodiments each of R and $R_1$-$R_8$ are independently —H, —OH, or a C1-C10 optionally substituted branched or straight chain alkyl group; and n is an integer from 0 to 24. In certain embodiments, at least one of $R_1$-$R_6$ is a tertiary butyl group. In certain other embodiments, $R_7$ and $R_8$ are tertiary butyl group. In certain other embodiments at least one of $R_7$ and $R_8$ is a methyl and the other is a tertiary butyl group. R' is —H, optionally substituted C1-C20 alkyl or optionally substituted aryl group.

In certain embodiments, the catalyst is a lewis acid, such as boric acid, meta boric acid or its derivatives soluble in organic solvents para-toluene, sulfonic acid, anhydrous sodium acetate, lithium acetate or lithium amide.

In certain embodiments, the disclosed catalysts are inexpensive, increase the rate of reaction and give a higher yield and better product color as compared to the currently used catalysts.

In certain embodiment, examples of suitable solvents include toluene, xylene, dichlorobenzene or a mixture of these solvents.

In certain embodiments the remainder of the reaction conditions are as described above for Scheme 1.

In another embodiment the present invention is a method of synthesizing a macromonomer represented by Structural Formula I, comprising the steps of:

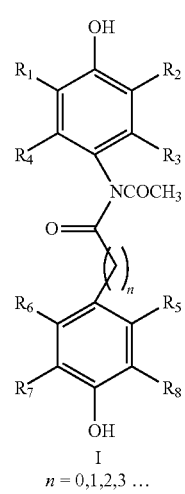

I
n = 0,1,2,3 ...

mixing sterically hindered phenol IA and aminophenol derivative III C in an organic solvent; or a mixture of organic solvents and heating the reaction mixture to reflux in the presence of a catalyst.

In certain embodiments each of R and $R_1$-$R_8$ are independently —H, —OH, or a C1-C10 optionally substituted branched or straight chain alkyl group; and n is an integer from 0 to 24. In certain embodiments, at least one of $R_1$-$R_6$ is a tertiary butyl group. In certain other embodiments, $R_7$ and $R_8$ are tertiary butyl group. In certain other embodiments at least one of $R_7$ and $R_8$ is a methyl and the other is a tertiary butyl group.

In certain embodiments, the catalyst is a lewis acid, such as boric acid, meta boric acid or its derivatives soluble in organic solvents para-toluene, sulfonic acid, anhydrous sodium acetate, lithium acetate or lithium amide.

In certain embodiment, examples of suitable solvents include toluene, xylene, dichlorobenzene or a mixture of these solvents.

In certain embodiments the remainder of the reaction conditions are as described above for Scheme 1.

In another embodiment the method of the present invention is represented by Scheme 6:

Scheme-5

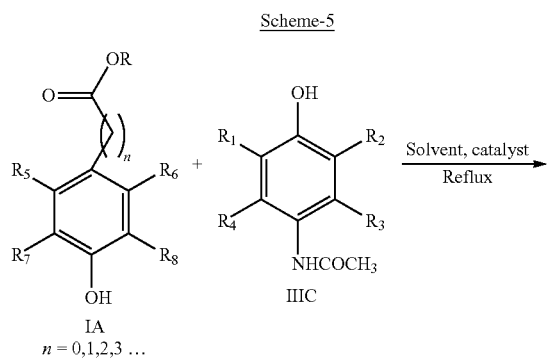

Scheme 2

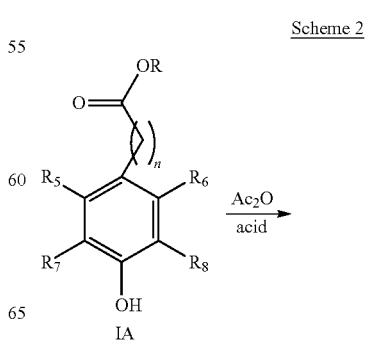

-continued

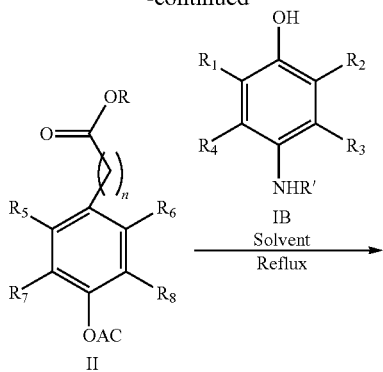

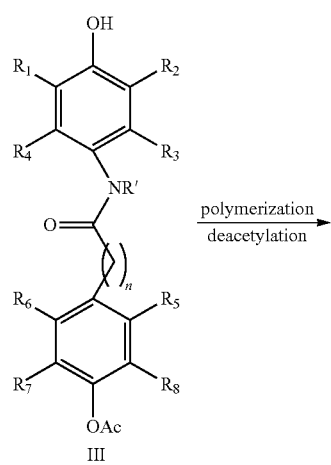

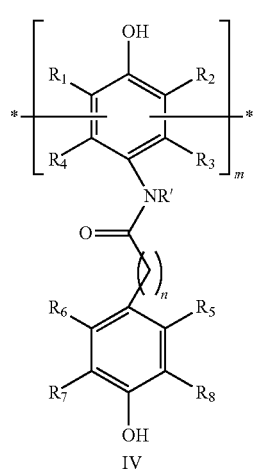

The reaction conditions are as described above for Scheme 2. The variables are as described above.

All the solvents used in the process can be recycled by separating the solvents from the reaction mixture using distillation. The compounds having Structures (I) are valuable antioxidants against oxidation, thermal degradation of organic compositions of matter. Such compositions are, for example, natural or synthetic polymers, functional liquids, such as lubricants, hydraulic fluids, paints and other finished products and goods.

In one embodiment the macromonomer is not:

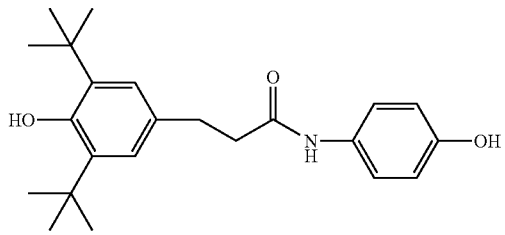

Antioxidant polymers of the present invention have two or more repeat units, preferably greater than about five repeat units. The molecular weight of the polymers disclosed herein can be generally selected to be appropriate for the desired application. Typically, the molecular weight can be greater than about 500 atomic mass units (amu) and less than about 2,000,000 amu, greater than about 1000 amu and less than about 100,000, greater than about 2,000 amu and less than about 10,000, or greater than about 2,000 amu and less than about 5,000 amu. For food or edible products (e.g., products fit for human consumption), the molecular weight can be advantageously selected to be large enough so that an antioxidant polymer cannot be absorbed by the gastrointestinal tract, such as greater than 1000 amu. For antioxidant polymers blended with a polymeric material, the molecule weight can be advantageously selected such that the rate of diffusion of the antioxidant polymer through the polymeric material can be slow relative to the expected lifetime of the polymeric material.

Antioxidant polymers of the present invention can be either homopolymers or copolymers. A copolymer preferably contains two or more or three or more different repeating monomer units, each of which has varying or identical antioxidant properties. The identity of the repeat units in a copolymer can be chosen to modify the antioxidant properties of the polymer as a whole, thereby giving a polymer with tunable properties. The second, third and/or further repeat units in a copolymer can be either a synthetic or natural antioxidant.

Antioxidant polymers of the present invention are typically insoluble in aqueous media. The solubility of the antioxidant polymers in non-aqueous media (e.g., oils) depends upon the molecular weight of the polymer, such that high molecular weight polymers are typically sparingly soluble in non-aqueous media. When an antioxidant polymer of the invention can be insoluble in a particular medium or substrate, it can be preferably well-mixed with that medium or substrate.

Disclosed is a catalyst-free method of preparing a macromonomer represented by Structural Formula I. The method comprises a step of mixing sterically hindered monomer IA and aminophenol IB in a suitable solvent and heating the reaction mixture to reflux as shown in Scheme I.

Scheme-1

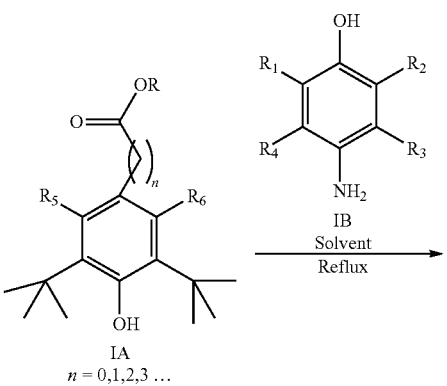

-continued

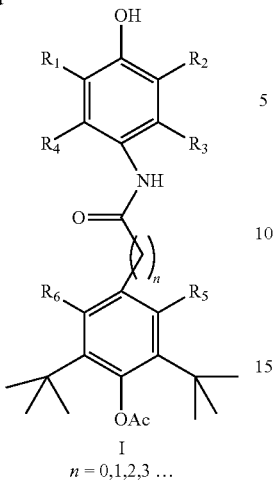

I
n = 0,1,2,3 ...

In Scheme I, R and R1-R6 are independently —H, —OH, or a C1-C10 alkyl group. n is an integer from 0 to 24.

A method for polymerizing an acetylated version of the macromonomer represented by Structural Formula I includes acetylating the phenol —OH of Structural Formula IA in acidic acetic anhydride; refluxing with amino phenol represented by Structural Formula IB in solvent to form a macromonomer represented by Structural Formula III; polymerization using an oxidative polymerization biocatalyst or biomimetic catalyst followed by deacetylation to form the antioxidant polymer represented by Structural Formula IV. The variables are as defined above.

Scheme-2

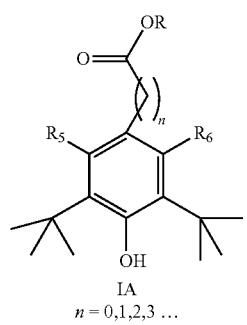

IA
n = 0,1,2,3 ...

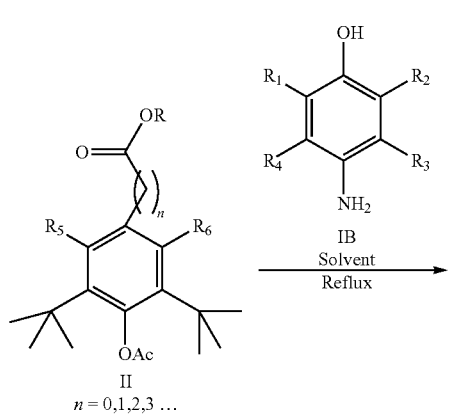

II
n = 0,1,2,3 ...

-continued

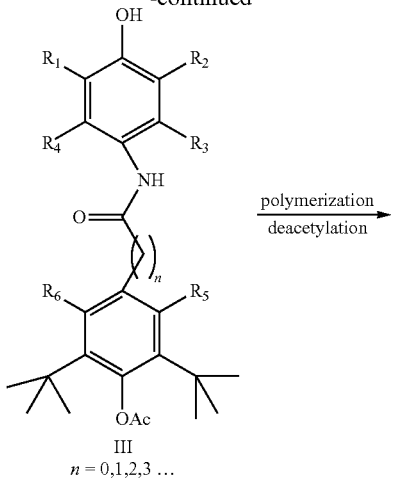

III
n = 0,1,2,3 ...

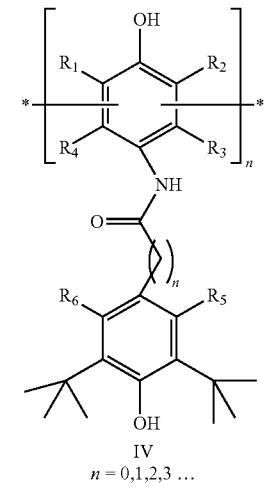

IV
n = 0,1,2,3 ...

A simple process for the synthesis of N- and phenol-based antioxidant macromonomers and their corresponding polymers The present invention relates to the synthesis of compounds containing nitrogen and hindered phenol functionalities of an aromatic amine and hindered phenol that could act as an oxidative stabilizer for organic materials, paints, lubricants elastomers, and in other applications. In particular, the present invention pertains to an improved, highly efficient and economical process for the synthesis of macromonomers having nitrogen containing moiety and sterically hindered phenols and their corresponding polymers.

Sterically hindered 3-hydroxyphenyl propionic acid esters and certain amide derivatives are known to be effective antioxidants for a wide range of organic substrates, particularly lubricants and polymers, protecting them from oxidative and thermal degradation. In general, these are prepared by the transesterification of corresponding carboxylic acid derivatives with various alcohols and amines. Various catalysts for this reaction are known, e.g. acids, bases, amines, metal alkoxides and also organotin compounds. It is economically advantageous if the reaction is carried out in the melt state without using any catalyst. Moreover, it is desirable to have a reaction process in which subsequent steps for separating the desired product from the reaction mixture is not required. In some cases the formation of discolored or stained products resulting from the presence of catalyst residues reaction is extremely undesirable. Certain end product properties, such as stability, or low toxicity, are some times negatively influenced if the trace levels of catalysts are in the final product. Therefore, an alternative process without involving the use of catalysts is desirable. In our earlier patent applications, 60/370,468, Ser. No. 10/408,679, and PCT/US03/10782, 60/590,575, 60/590,646 it was demonstrated the synthesis of poly (sterically hindered phenol) antioxidants from substituted phenols. These macromonomer and polymeric antioxidants showed significantly improved antioxidant activities in cooking oils, plastics, lubricants and other industrial applications compared to currently used (monomeric) antioxidants. The present invention is related to the synthesis of antioxidant macromonomers and their corresponding polymers without or minimal use of catalysts The present invention relates to a process for the preparation of a macromonomer of Structure I:

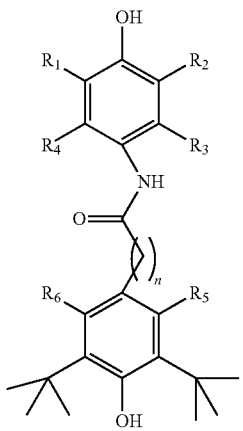

I

The novel one-step process for the synthesis of macromonomer I does not require any catalyst and can simply made by mixing the two component in a suitable solvent and heating the reaction mixture to reflux as shown in Scheme I.

Scheme-1

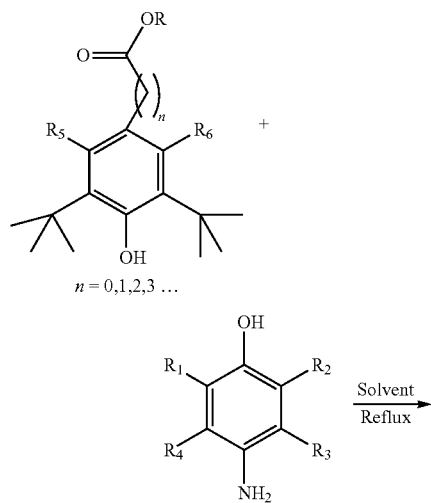

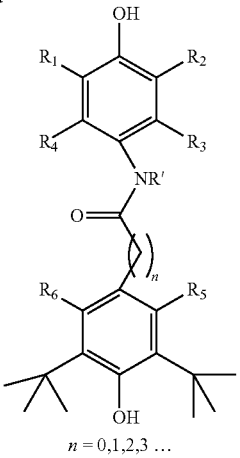

Define R1-R6 could independently be OH or H.

The one pot synthetic process involves the mixing of sterically hindered phenolic acid derivatives, preferably 3-(3,5-di-tertbutyl, 4-hydroxyphenyl)propionic acid, 3,5-di-tertbutyl, 4-hydroxybenzoic acid or their lower alkyl esters with substituted amino phenols most preferably 4-amino phenol in a suitable solvent. The solvent used in the this process may be one or mixture solvents. The prefered solvent for the process is a mixture of toluene and N-methylpyrrolidone (NMP) in a prefered ratio of 10:1. The prefered method of this disclosure is the mixing of equimoles of 3-(3,5-di-tertbutyl, 4-hydroxyphenyl)propionic acid and 4-amino phenol in a 10:1 mixture of toluene and NMP and refluxing the reaction mixture at 100° C. using a Dean's Stark appratus to remove the water that is produced in the reaction. The process is very simple and highly efficient, economical and do not require any catalyst.

Antioxidant polymers of the present invention can be branched or linear, but are preferably linear. Branched antioxidant polymers can only be formed from benzene molecules having three or fewer substituents (e.g., three or more hydrogen atoms).

Antioxidant polymers of the present invention can be present in a wide variety of compositions where free radical mediated oxidation leads to deterioration of the quality of the composition, including edible products such as oils, foods (e.g., meat products, dairy products, cereals, etc.), and other products containing fats or other compounds subject to oxidation. Antioxidant polymers can also be present in plastics and other polymers, elastomers (e.g., natural or synthetic rubber), petroleum products (e.g., fossil fuels such as gasoline, kerosene, diesel oil, heating oil, propane, jet fuel), lubricants, paints, pigments or other colored items, soaps and cosmetics (e.g., creams, lotions, hair products). The antioxidant polymers can be used to coat a metal as a rust and corrosion inhibitor. Antioxidant polymers additionally can protect antioxidant vitamins (Vitamin A, Vitamin C, Vitamin E) and pharmaceutical products from degradation. In food products, the antioxidant polymers can prevent rancidity. In plastics, the antioxidant polymers can prevent the plastic from becoming brittle and cracking.

Antioxidant polymers of the present invention can be added to oils to prolong their shelf life and properties. These oils can be formulated as vegetable shortening or margarine. Oils generally come from plant sources and include cottonseed oil, linseed oil, olive oil, palm oil, corn oil, peanut oil, soybean oil, castor oil, coconut oil, safflower oil, sunflower oil, canola (rapeseed) oil and sesame oil. These oils contain one or more unsaturated fatty acids such as caproleic acid, palmitoleic acid, oleic acid, vaccenic acid, elaidic acid, brassidic acid, erucic acid, nervonic acid, linoleic acid, eleosteric acid, alpha-linolenic acid, gamma-linolenic acid, and arachidonic acid, or partially hydrogenated or trans-hydrogenated variants thereof. Antioxidant polymers of the present invention are also advantageously added to food or other consumable products containing one or more of these fatty acids.

The shelf life of many materials and substances contained within the materials, such as packaging materials, are enhanced by the presence of an antioxidant polymer of the present invention. The addition of an antioxidant polymer to a packaging material is believed to provide additional protection to the product contained inside the package. In addition, the properties of many packaging materials themselves, particularly polymers, are enhanced by the presence of an antioxidant regardless of the application (i.e., not limited to use in packaging). Common examples of packaging materials include paper, cardboard and various plastics and polymers. A packaging material can be coated with an antioxidant polymer (e.g., by spraying the antioxidant polymer or by applying as a thin film coating), blended with or mixed with an antioxidant polymer (particularly for polymers), or otherwise have an antioxidant polymer present within it. In one example, a thermoplastic such as polyethylene, polypropylene or polystyrene can be melted in the presence of an antioxidant polymer in order to minimize its degradation during the polymer processing. An antioxidant polymer can also be co-extruded with a polymeric material.

The term "alkyl" as used herein means a saturated straight-chain, branched or cyclic hydrocarbon. When straight-chained or branched, an alkyl group is typically C1-C8, more typically C1-C6; when cyclic, an alkyl group is typically C3-C12, more typically C3-C7 alkyl ester. Examples of alkyl groups include methyl, ethyl, n-propyl, iso-propyl, n-butyl, sec-butyl and tert-butyl and 1,1-dimethylhexyl.

The term "alkoxy" as used herein is represented by —OR, wherein R is an alkyl group as defined above.

The term "carbonyl" as used herein is represented by —C(=O)R, wherein R is an alkyl group as defined above.

The term "alkoxycarbonyl" as used herein is represented by —C(=O)OR, wherein R is an alkyl group as defined above.

The term "aromatic group" includes carbocyclic aromatic rings and heteroaryl rings. The term "aromatic group" may be used interchangeably with the terms "aryl"; "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which a carbocyclic aromatic ring is fused to one or more aromatic rings (carbocyclic aromatic or heteroaromatic)r. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring (carbocyclic or heterocyclic). Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, oxadiazolyl, oxadiazolyl, 2-oxazolyl, 4-oxazolyl, 5-oxazolyl, N-pyrazolyl, 3-pyrazolyl, 4-pyrazolyl, 5-pyrazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-thiazolyl, 4-thiazolyl, 5-thiazolyl, triazolyl, tetrazolyl, 2-thienyl, 3-thienyl, carbazolyl, benzothienyl, benzofuranyl, indolyl, quinolinyl, benzothiazole, benzooxazole, benzimidazolyl, isoquinolinyl and isoindolyl. Also included within the scope of the term "heteroaryl", as it is used herein, is a group in which an aromatic ring is fused to one or more non-aromatic rings (carbocyclic or heterocyclic).

The term non-aromatic heterocyclic group used alone or as part of a larger moiety refers to non-aromatic heterocyclic ring groups having three to fourteen members, including monocyclic heterocyclcic rings and polycyclic rings in which a monocyclic ring is fused to one or more other non-aromatic carbocyclic or heterocyclic ring or aromatic ring (carbocyclic or heterocyclic). Heterocyclic groups have one or more ring heteroatoms, and can be saturated or unsaturated. Examples of heterocyclic groups include piperidinyl, piperizinyl, pyrrolidinyl, pyrazolidinyl, imidazolidinyl, tetrahydroquinolinyl, inodolinyl, isoindolinyl, tetrahydrofuranyl, oxazolidinyl, thiazolidinyl, dioxolanyl, dithiolanyl, tetrahydropyranyl, dihydropyranyl, azepanyl aNd azetidinyl The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group, as defined below.

As used herein the term non-aromatic carbocyclic ring as used alone or as part of a larger moiety refers to a non-aromatic carbon containing ring which can be saturated or unsaturated having three to fourteen atoms including monocyclic and polycyclic rings in which the carbocyclic ring can be fused to one or more non-aromatic carbocyclic or heterocyclic rings or one or more aromatic (carbocyclic or heterocyclic) rings An optionally substituted aryl group as defined herein may contain one or more substitutable ring atoms, such as carbon or nitrogen ring atoms. Examples of suitable substituents on a substitutable ring carbon atom of an aryl group include halogen (e.g., —Br, Cl, I and F), —OH, C1-C4 alkyl, C1-C4 haloalkyl, —NO₂, C1-C4 alkoxy, C1-C4 haloalkoxy, —CN, —NH₂, C1-C4 alkylamino, C1-C4 dialkylamino, —C(O)NH₂, —C(O)NH(C1-C4 alkyl), —C(O)(C1-C4 alkyl), —OC(O)(C1-C4 alkyl), —OC(O)(aryl), —OC(O)(substituted aryl), —OC(O)(aralkyl), —OC(O)(substituted aralkyl), —NHC(O)H, —NHC(O)(C1-C4 alkyl), —C(O)N(C1-C4 alkyl)₂, —NHC(O)O—(C1-C4 alkyl), —C(O)OH, —C(O)O—(C1-C4 alkyl), —NHC(O)NH₂, —NHC(O)NH(C1-C4 alkyl), —NHC(O)N(C1-C4 alkyl)₂, —NH—C(=NH)NH₂, —SO₂NH₂—SO₂NH(C1-C3alkyl), —SO₂N(C1-C3alkyl)₂, NHSO₂H, NHSO₂(C1-C4 alkyl) and optionally substituted aryl. Preferred substituents on aryl groups are as defined throughout the specification. In certain embodiments aryl groups are unsubstituted.

Examples of suitable substituents on a substitutable ring nitrogen atom of an aryl group include C1-C4 alkyl, $NH_2$, C1-C4 alkylamino, C1-C4 dialkylamino, —C(O)$NH_2$, —C(O)NH(C1-C4 alkyl), —C(O)(C1-C4 alkyl), —$CO_2$R, —C(O)C(O)R, —C(O)$CH_3$, —C(O)OH, —C(O)O—(C1-C4 alkyl), —$SO_2NH_2$—$SO_2$NH(C1-C3alkyl), —$SO_2$N(C1-C3alkyl)$_2$, $NHSO_2$H, $NHSO_2$(C1-C4 alkyl), —C(=S)$NH_2$, —C(=S)NH(C1-C4 alkyl), —C(=S)N(C1-C4 alkyl)$_2$, —C(=NH)—N(H)$_2$, —C(=NH)—NH(C1-C4 alkyl) and —C(=NH)—N(C1-C4 alkyl)$_2$.

Further, examples of suitable substituents on an alkyl, aryl or acyl group may include, for example, halogen (—Br, —Cl, —I and —F), —OR$_a$, —CN, —$NO_2$, —N(R$_a$)$_2$, —COOR$_a$, —CON(R$_a$)$_2$, —SO$_k$R$_a$ (k is 0, 1 or 2) and —NH—C(=NH)—$NH_2$. An alkyl group can also have =O or =S as a substituent. Each R$_a$ is independently —H, an alkyl group, a substituted alkyl group, a benzyl group, a substituted benzyl group, an aryl group or a substituted aryl group. A substituted benzylic group or aryl group can also have an alkyl or substituted alkyl group as a substituent. A substituted alkyl group can also have a benzyl, substituted benzyl, aryl or substituted aryl group as a substituent. A substituted alkyl, substituted aryl or substituted acyl group can have more than one substituent.

An optionally substituted alkyl group or non-aromatic carbocyclic or heterocyclic group as defined herein may contain one or more substituents. Examples of suitable substituents for an alkyl group include those listed above for a substitutable carbon of an aryl and the following: =O, =S, =NNHR, =NN(R)$_2$, =NNHC(O)R, =NNHCO$_2$(alkyl), =NNSO$_2$(alkyl), =NR, spiro cycloalkyl group or fused cycloalkyl group. R** in each occurrence, independently is —H or C1-C6 alkyl. Preferred substituents on alkyl groups are as defined throughout the specification. In certain embodiments optionally substituted alkyl groups are unsubstituted.

A "spiro cycloalkyl" group is a cycloalkyl group which shares one ring carbon atom with a carbon atom in an alkylene group or alkyl group, wherein the carbon atom being shared in the alkyl group is not a terminal carbon atom.

Without wishing to be bound by any theory or limited to any mechanism it is believed that macromolecular antioxidants and polymeric macromolecular antioxidants of the present invention exploit the differences in activities (ks, equilibrium constant) of, for example, homo-or hetero-type antioxidant moieties. Antioxidant moieties include, for example, hindered phenolic groups, unhindered phenolic groups, aminic groups and thioester groups, etc. of which there can be one or more present in each macromolecular antioxidant molecule. As used herein a homo-type antioxidant macromolecule comprises antioxidant moieties which are all same, for example, hindered phenolic, —OH groups. As used herein a hetero-type antioxidant macromolecule comprises at least one different type of moiety, for example, hindered phenolic and aminic groups in the one macromolecule.

This difference in activities can be the result of, for example, the substitutions on neighboring carbons or the local chemical or physical environment (for example, due to electrochemical or stereochemical factors) which can be due in part to the macromolecular nature of molecules.

In one embodiment of the present invention, a series of macromolecular antioxidant moieties of the present invention with different chemical structures can be represented by W1H, W2H, W3H, . . . to WnH. In one embodiment of the present invention, two types of antioxidant moieties of the present invention can be represented by: W1H and W2H. In certain embodiments W1H and W2H can have rate constants of k1 and k2 respectively. The reactions involving these moieties and peroxyl radicals can be represented as:

   (1)

   (2)

where ROO. is a peroxyl radical resulting from, for example, initiation steps involving oxidation activity, for example:

   (3)

   (4)

In one particular embodiment of the present invention k1>>k2 in equations (1) and (2). As a result, the reactions would take place in such a way that there is a decrease in concentration of W1. free radicals due their participation in the regeneration of active moiety W2H in the molecule according equation (5):

   (5) (transfer equilibrium)

This transfer mechanism may take place either in intra-or inter-molecular macromolecules. The transfer mechanism (5) could take place between moieties residing on the same macromolecule (intra-type) or residing on different macromolecules (inter-type).

In certain embodiments of the present invention, the antioxidant properties described immediately above (equation 5) of the macromolecular antioxidants and polymeric macromolecular antioxidants of the present invention result in advantages including, but not limited to:
  a) Consumption of free radicals W1. according to equation (5) can result in a decrease of reactions of W1. with hydroperoxides and hydrocarbons (RH).
  b) The regeneration of W1H provides extended protection of materials. This is a generous benefit to sacrificial type of antioxidants that are used today. Regeneration of W1H assists in combating the oxidation process The increase in the concentration of antioxidant moieties W1H (according to equation 5) extends the shelf life of materials.

In certain embodiments of the present invention, the following items are of significant interest for enhanced antioxidant activity in the design of the macromolecular antioxidants and polymeric macromolecular antioxidants of the present invention:
  a) The activity of proposed macromolecular antioxidant is dependent on the regeneration of W1H in equation (5) either through inter-or intra-molecular activities involving homo-or hetero-type antioxidant moieties.
  b) Depending on the rates constants of W1H and W2H it is possible to achieve performance enhancements by many multiples and not just incremental improvements.

In certain embodiments of the present invention, more than two types of antioxidant moieties with different rate constants are used in the methods of the present invention.

The entire contents of each of the following are incorporated herein by reference.
Provisional Patent Application No. 60/632,893, filed Dec. 3, 2004, Title: Process For The Synthesis Of Polyalkylphenol Antioxidants, by Suizhou Yang, et al;

11/292,813; filed Dec. 2, 2005, Title: Process for the Synthesis of Polyalkylphenol Antioxidants, by Suizhou Yang, et al;

Provisional Patent Application No. 60/633,197, filed Dec. 3, 2004, Title: Synthesis Of Sterically Hindered Phenol Based Macromolecular Antioxidants, by Ashish Dhawan, et al.;

11/293,050; filed Dec. 2, 2005, Title: Synthesis Of Sterically Hindered Phenol Based Macromolecular Antioxidants, by Ashish Dhawan, et al.;

U.S. Provisional Application No. 60/633,252 filed Dec. 3, 2004, Title: ONE POT PROCESS FOR MAKING POLYMERIC ANTIOXIDANTS by Kumar, et al.

11/293,049, filed Dec. 2, 2005, Title: ONE POT PROCESS FOR MAKING POLYMERIC ANTIOXIDANTS by Kumar, et al.

patent application Ser. No. 11/184,724, filed Jul. 19, 2005, Title: Anti-Oxidant Macromonomers And Polymers And Methods Of Making And Using The Same, by Ashok L. Cholli;

patent application Ser. No. 11/184,716, filed Jul. 19, 2005, Title: Anti-Oxidant Macromonomers And Polymers And Methods Of Making And Using The Same, by Ashok L. Cholli;

Provisional Patent Application No. 60/655,169, filed Feb. 2, 2005, Title: Nitrogen And Hindered Phenol Containing Dual Functional Macromolecules: Synthesis And Their Antioxidant Performances In Organic Materials, by Rajesh Kumar, et al.

Provisional Patent Application No. 60/655,169, filed Mar. 25, 2005, Title: Alkylated Macromolecular Antioxidants And Methods Of Making, And Using The Same, by Rajesh Kumar, et al.

Provisional Patent Application No. 60/731,125, filed Oct. 27, 2005, Title: Macromolecular Antioxidants And Polymeric Macromolecular Antioxidants, by Ashok L. Cholli, et al.

Provisional Patent Application No. 60/731,021, filed Oct. 27, 2005, Title: Macromolecular Antioxidants Based On Sterically Hindered Phenols And Phosphites, by Ashok L. Cholli, et al.

Provisional Patent Application, filed Dec. 2, 2005, Title: Lubricant Composition, by Kumar, Rajesh, et al.

Provisional Patent Application No. 60/731,325, filed Oct. 27, 2005, Title: Stabilized Polyolefin Composition, by Kumar, Rajesh, et al.

patent application Ser. No. 11/040,193, filed Jan. 21 2005, Title: Post-Coupling Synthetic Approach For Polymeric Antioxidants, by Ashok L. Choll, et al.;

patent application No.: PCT/US2005/001948, filed Jan. 21, 2005, Title: Post-Coupling Synthetic Approach For Polymeric Antioxidants, by Ashok L. Cholli et al.;

patent application No.: PCT/US2005/001946, filed Jan. 21, 2005, Title: Polymeric Antioxidants, by Ashok L. Choll, et al.;

patent application No.: PCT/US03/10782, filed Apr. 4, 2003, Title: Polymeric Antioxidants, by Ashok L. Choll, et al.;

patent application Ser. No. 10/761,933, filed Jan. 21, 2004, Title: Polymeric Antioxidants, by Ashish Dhawan, et al.;

patent application Ser. No. 10/408,679, filed Apr. 4, 2003, Title: Polymeric Antioxidants, by Ashok L. Choll, et al.;

Tertiary Butoxy Derivatives of Phenol. (Jan Pospisil and Ludek Taimr). (1964), 2 pp. CS 111291

A New Synthesis of aryl tert-butyl Ethers. Masada, Hiromitsu; Oishi, Yutaka. Fac. Eng., Kanazawa Univ., Kanazawa, Japan. Chemistry Letters (1978), (1), 57-8.

Simple Synthesis of the tert-butyl Ether of Phenol. Ol'dekop, Yu. A.; Maier, N. A.; Erdman, A. A.; Shirokii, V. L.; Zubreichuk, Z. P.; Beresnevich, L. B. Inst. Fiz.-Org. Khim., Minsk, USSR. Zhurnal Obshchei Khimii (1980), 50(2), 475-6.

New Method for the Williamson Ether Synthesis Using tert-alkyl Halides in Nonpolar Solvents. Masada, Hiromitsu; Mikuchi, Fumio; Doi, Yasuo; Hayashi, Akira. Dep. Chem. Chem. Eng., Kanazawa Univ., Kanazawa, Japan. Nippon Kagaku Kaishi (1995), (2), 164-6.

New Heterogeneous Williamson Synthesis of Ethers Using tert-alkyl Substrates. Masada, Hiromitsu; Doi, Yasuo; Mikuchi, Fumio; Keiko, Kigoshi. Faculty Eng., Kanazawa Univ., Kanazawa, Japan. Nippon Kagaku Kaishi (1996), (3), 275-82.

Preparation of Aromatic Tertiary Ethers. Tanaka, Masato; Reddy, Nagaveri Prabacal. (Agency of Industrial Sciences and Technology, Japan). Jpn. Kokai Tokkyo Koho (1999), 3 pp. JP 080063.

Preparation of Aromatic Ethers. Watanabe, Makoto; Koie, Yasuyuki. (Tosoh Corp., Japan). Jpn. Kokai Tokkyo Koho (1999), 10 pp. JP 11158103.

o-Alkylated phenols. Firth, Bruce E.; Rosen, Terry J. (UOP Inc., USA). U.S. Pat. No. 4,447,657 (1984), 4 pp.

2-Tert-Butyl-4-alkoxy-and -4-hydroxyphenols. Firth, Bruce E.; Rosen, Terry J. (UOP Inc., USA). U.S. Pat. No. 4,465,871 (1984), 4 pp.

Conversion of Alkyl Phenyl Ether to Alkylphenol. Klicker, James D. (Borg-Warner Corp., USA). U.S. Pat. No. 4,283,572 (1981), 3 pp.

O. N. Tsevktov, K. D. Kovenev, *Int. J. Chem. Eng.* 6 (1966), 328.

Sartori Giovanni, Franca Bigi et al., *Chem. Ind.* (London), 1985 (22) 762-763.

V. A. Koshchii, Ya. B Kozlikovskii, A. A Matyusha, Zh. *Org. Khim.* 24(7), 1988, 1508-1512.

Gokul K. Chandra, M. M. Sharma, *Catal. Lett.* 19(4), 1993, 309-317.

Sakthivel, Ayyamperumal; Saritha, Nellutla; Selvam, Parasuraman, *Catal. Lett.* 72(3), 2001, 225-228.

V. Quaschning, J. Deutsch, P. Druska, H. J. Niclas and E. Kemnitz. *J. Catal.* 177 (1998), p. 164.

S. K. Badamali, S. Sakthivel and P. Selvam. *Catal. Today* 63 (2000), p. 291.

A. Heidekum, M. A. Hamm and F. Hoelderich. *J. Catal.* 188 (1999), p. 230.

Y. Kamitori, M. Hojo, R. Matsuda, T. Izumi and S. Tsukamoto. *J. Org. Chem.* 49 (1984), p. 4165.

E. Armengol, A. Corma, H. García and J. Primo. *Appl. Catal. A* 149 (1997), p. 411.

J. M. Lalancette, M. J. Fournier and R. Thiffault. *Can. J Chem.* 52 (1974), p. 589.

Japanese Patent No. JP 145002980, 1970.

Japanese Patent No. 44028850, 1969.

Japanese Patent No. 44024274, 1969.

EXEMPLIFICATION

Example 1

One Pot Macromonomer Synthesis at Large Scale 3-(3,5-di-tertbutyl, 4-hydroxyphenyl)propionic acid (1.47 Kg) and 4-amino phenol (0.635 Kg) were dissolved in a 10:1 mixture of toluene and N-methylpyrrolidone (NMP, 5 L). The reaction mixture was refluxed at 100° C. using a Dean Stark apparatus equipped with a condenser. The water formed during reaction was removed by its azeotropic distillation with toluene. After completion, the solvent was removed by distillation and ice-cold water added and refluxed. The reaction mixture was cooled to room temperature and product was isolated by filtration.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of synthesizing a macromonomer represented by Structural Formula I, comprising the steps of:
   a) combining sterically hindered phenol IA and aminophenol IB;
   b) heating the combination of step a) to reflux to create a macromonomer represented by Structural Formula I;

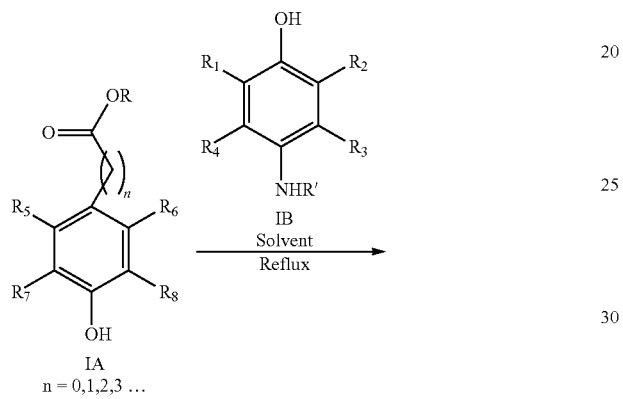

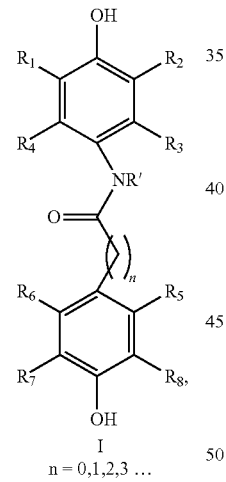

wherein:
   each of $R_1$-$R_4$ are independently —H or —OH;
   each of R and $R_5$-$R_8$ are independently —H, —OH, or a C1-C10 alkyl group;
   R' is —H, optionally substituted C1-C20 alkyl or optionally substituted aryl group; and
   n is an integer from 0 to 24.

2. The method of claim 1, wherein one of $R_7$ and $R_8$ is a tertiary butyl group and the other is a methyl group.

3. The method of claim 1, wherein both $R_7$ and $R_8$ are tertiary butyl groups.

4. The method of claim 1, wherein the combination of step a) is heated to between 30 and 150° C.

5. The method of claim 4, wherein the combination of step a) is heated to between 80 and 110° C.

6. The method of claim 5, wherein the sterically hindered phenol IA and aminophenol IB are combined in step a) in an organic solvent, wherein the organic solvent is a mixture of toluene and N-methylpyrrolidone.

7. A method for synthesizing an antioxidant polymer represented by Structural Formula IV, comprising the steps of:
   a) acetylating a hydroxyl group of a compound represented by Structural Formula IA to create an acetylated phenol represented by Structural Formula II;
   b) combining the acetlylated phenol represented by Structural Formula II and amino phenol represented by Structural Formula IB
   c) heating the combination of step b) to reflux to create a macromonomer represented by Structural Formula III;
   d) polymerizing the macromonomer represented by Structural Formula III using an oxidative polymerization followed by acidic deacetylation to form the antioxidant polymer represented by Structural Formula IV;

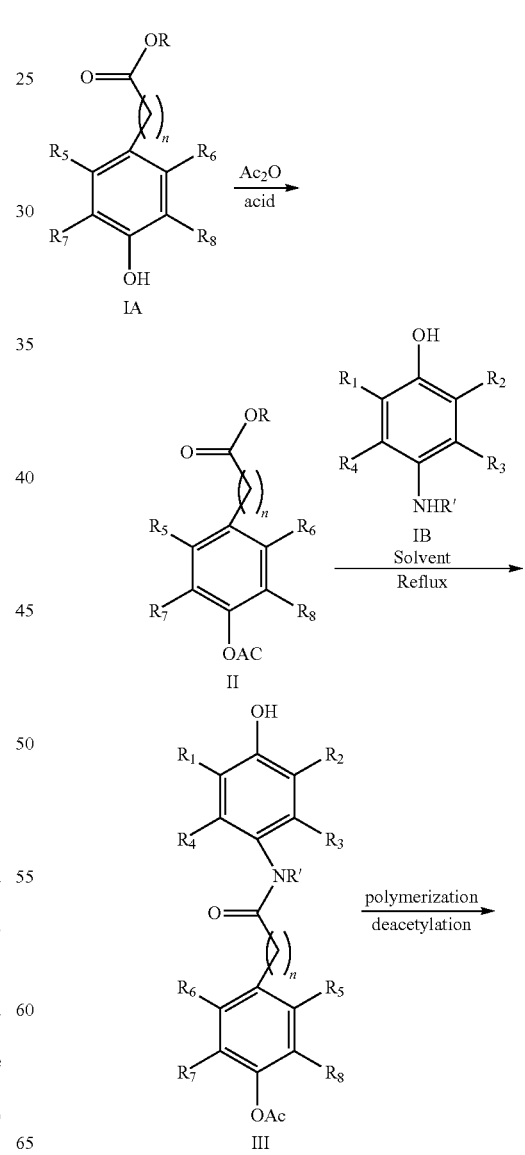

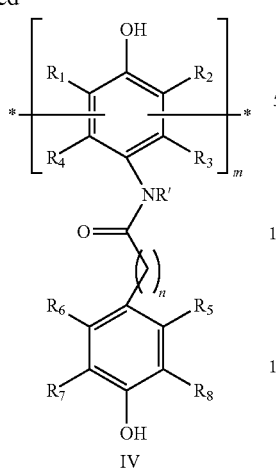

IV wherein:

each of $R_1$-$R_4$ are independently —H or —OH;

each of R and $R_5$-$R_8$ are independently —H, —OH, or a C1-C10 alkyl group;

R' is —H, optionally substituted C1-C20 alkyl or optionally substituted aryl group;

n is an integer from 0 to 24; and m is an integer equal to 2 or greater.

8. The method of claim 4, wherein one of $R_7$ and $R_8$ is a tertiary butyl group and the other is a methyl group.

9. The method of claim 4, wherein both $R_7$ and $R_8$ are tertiary butyl groups.

10. The method of claim 7, wherein the oxidative polymerization catalyst is a biocatalyst or biomimetic catalyst selected from Iron(II)-salen complexes, horseradish peroxidase (HRP), soybean peroxidase (SBP), hematin, laccase, tyroniase, and a tyroniase-model complex.

11. The method of claim 7, wherein the oxidative polymerization catalyst is an inorganic or organometallic catalyst.

12. The method of claim 6, wherein the combination of step a) is heated to between 30 and 150° C.

13. The method of claim 12, wherein the combination of step a) is heated to between 80 and 110° C.

14. The method of claim 13, wherein the acetylated phenol represented by Structural Formula II and amino phenol represented by Structural Formula IB are combined in step b) in an organic solvent wherein the organic solvent is a mixture of toluene and N-methylpyrrolidone.

15. A method of synthesizing a macromonomer represented by Structural Formula I, comprising the steps of:

a) combining sterically hindered phenol IA and aminophenol IB;

b) heating the combination of step a) to reflux in the presence of a catalyst selected from the group comprising boric acid, meta boric acid, para-toluene, sulfonic acid, anhydrous sodium acetate, lithium acetate and lithium amide to create a macromonomer represented by Structural Formula I;

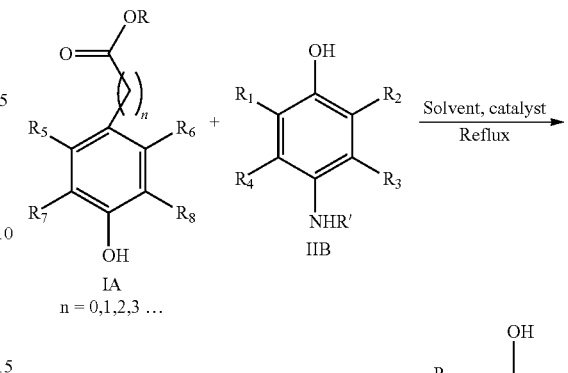

IA
n = 0,1,2,3 ...

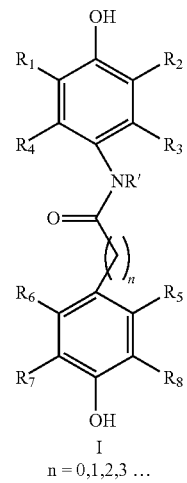

I
n = 0,1,2,3 ...

wherein:

each of $R_1$-$R_4$ are independently —H or —OH;

each of R and $R_5$-$R_8$ are independently —H, —OH, or a C1-C10 alkyl group;

R' is —H, optionally substituted C1-C20 alkyl or optionally substituted aryl group; and n is an integer from 0 to 24.

16. A method of synthesizing a macromonomer represented by Structural Formula I, comprising the steps of:

a) combining sterically hindered phenol IA and IIIC in an organic solvent;

b) heating the combination of step a) to reflux in the presence of a catalyst selected from the group comprising boric acid, meta boric acid, para-toluene, sulfonic acid, anhydrous sodium acetate, lithium acetate and lithium amide to create a macromonomer represented by Structural Formula I;

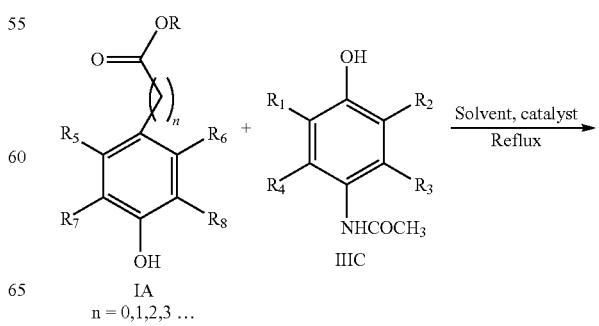

IA
n = 0,1,2,3 ...

-continued

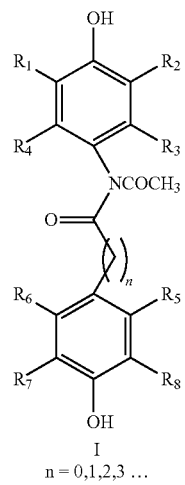

I
n = 0,1,2,3 ...

wherein:
each of $R_1$-$R_4$ are independently —H or —OH;
each of R and $R_5$-$R_8$ are independently —H, —OH, or a C1-C10 alkyl group;
R' is —H, optionally substituted C1-C20 alkyl or optionally substituted aryl group; and
n is an integer from 0 to 24.

17. The method of claim 15, wherein one of $R_7$ and $R_8$ is a tertiary butyl group and the other is a methyl group.

18. The method of claim 15, wherein both $R_7$ and $R_8$ are tertiary butyl groups.

19. The method of claim 16, wherein one of $R_7$ and $R_8$ is a tertiary butyl group and the other is a methyl group.

20. The method of claim 16, wherein both $R_7$ and $R_8$ are tertiary butyl groups.

* * * * *

UNITED STATES PATENT AND TRADEMARK OFFICE
CERTIFICATE OF CORRECTION

PATENT NO.        : 7,902,317 B2
APPLICATION NO.   : 11/293844
DATED             : March 8, 2011
INVENTOR(S)       : Rajesh Kumar, Suizhou Yang and Ashok L. Cholli Page 1 of 1

It is certified that error appears in the above-identified patent and that said Letters Patent is hereby corrected as shown below:

Claim 15, Column 30, line 11, second molecule, please delete "IIB" and insert --IB--.

Signed and Sealed this
Twenty-fourth Day of May, 2011

David J. Kappos
*Director of the United States Patent and Trademark Office*